(12) United States Patent
Lee et al.

(10) Patent No.: US 11,362,286 B2
(45) Date of Patent: Jun. 14, 2022

(54) ORGANIC ELECTROLUMINESCENCE DEVICE AND HETEROCYCLIC COMPOUND FOR ORGANIC ELECTROLUMINESCENCE DEVICE

(71) Applicant: Samsung Display Co., Ltd., Yongin-si (KR)

(72) Inventors: Jungsub Lee, Hwaseong-si (KR); Hyein Jeong, Suwon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 654 days.

(21) Appl. No.: 16/268,276

(22) Filed: Feb. 5, 2019

(65) Prior Publication Data
US 2019/0252626 A1  Aug. 15, 2019

(30) Foreign Application Priority Data
Feb. 12, 2018 (KR) .............. 10-2018-0017

(51) Int. Cl.
*H01L 51/00* (2006.01)
*C07D 417/10* (2006.01)
(Continued)

(52) U.S. Cl.
CPC ........ *H01L 51/0074* (2013.01); *C07D 401/10* (2013.01); *C07D 401/14* (2013.01); *C07D 413/10* (2013.01); *C07D 413/14* (2013.01); *C07D 417/10* (2013.01); *C07D 417/14* (2013.01); *C09K 11/06* (2013.01); *H01L 51/0067* (2013.01); *H01L 51/0071* (2013.01); *H01L 51/0072* (2013.01); *C09K 2211/1018* (2013.01); *H01L 51/001* (2013.01); *H01L 51/5016* (2013.01); *H01L 51/5056* (2013.01); *H01L 51/5072* (2013.01); *H01L 51/5088* (2013.01); *H01L 51/5092* (2013.01)

(58) Field of Classification Search
CPC .. C07D 401/10; C07D 401/14; C07D 413/10; C07D 413/14; C07D 417/10; C07D 417/14; C09K 11/06; C09K 2211/1018
See application file for complete search history.

(56) References Cited

U.S. PATENT DOCUMENTS 9,899,619 B2  2/2018 Lee et al.
9,947,876 B2  4/2018 Kawamura et al.
(Continued)

FOREIGN PATENT DOCUMENTS

| CN | 106397423 A | * | 2/2017 |
| CN | 108218850 A | * | 6/2018 |
| KR | 10-2016-0095014 A | | 8/2016 |
| KR | 10-2017-0040011 A | | 4/2017 |
| KR | 10-1752573 B1 | | 6/2017 |
| KR | 10-2017-0083960 A | | 7/2017 |

(Continued)

*Primary Examiner* — Alexander R Pagano
(74) *Attorney, Agent, or Firm* — Lewis Roca Rothgerber Christie LLP

(57) ABSTRACT

An organic electroluminescence device includes a first electrode, a hole transport region disposed on the first electrode, a light emitting layer disposed on the hole transport region, an electron transport region disposed on the light emitting layer, and a second electrode disposed on the electron transport region. The light emitting layer includes a heterocyclic compound represented by Formula 1 below. In Formula 1, $D_1$ and $D_2$ are each independently represented by Formula 2 below, and A is represented by any one of Formulas 3-1 to 3-3 below.

$$D_1\text{-}A\text{-}D_2 \qquad \text{Formula 1}$$

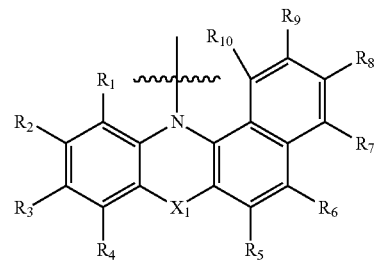

Formula 2

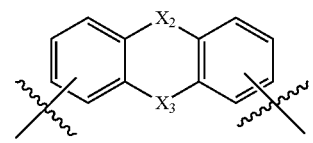

Formula 3-1

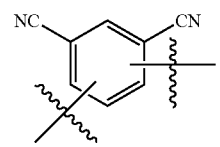

Formula 3-2

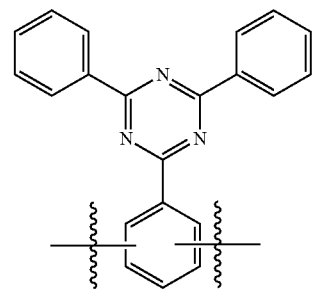

Formula 3-3

20 Claims, 1 Drawing Sheet

(51) Int. Cl.
   *C07D 413/14*   (2006.01)
   *C07D 413/10*   (2006.01)
   *C07D 401/10*   (2006.01)
   *C07D 401/14*   (2006.01)
   *C09K 11/06*    (2006.01)
   *C07D 417/14*   (2006.01)
   *H01L 51/50*    (2006.01)

(56) References Cited

U.S. PATENT DOCUMENTS

| | | | |
|---|---|---|---|
| 10,615,348 B2 * | 4/2020 | Miyazaki | H01L 51/0072 |
| 2016/0293853 A1 * | 10/2016 | Zeng | H01L 51/0067 |
| 2016/0380205 A1 | 12/2016 | Adachi et al. | |
| 2019/0393422 A1 * | 12/2019 | Sakamoto | H01L 51/0067 |
| 2021/0098708 A1 * | 4/2021 | Kim | C09K 11/06 |

FOREIGN PATENT DOCUMENTS

| | | |
|---|---|---|
| KR | 10-1820208 B1 | 1/2018 |
| WO | WO 2016/017684 A1 | 2/2016 |

\* cited by examiner

ORGANIC ELECTROLUMINESCENCE DEVICE AND HETEROCYCLIC COMPOUND FOR ORGANIC ELECTROLUMINESCENCE DEVICE

CROSS-REFERENCE TO RELATED APPLICATION

This patent application claims priority to and the benefit of Korean Patent Application No. 10-2018-0017147, filed on Feb. 12, 2018, in the Korean Intellectual Property Office, the entire content of which is hereby incorporated by reference.

BACKGROUND

1. Field

The present disclosure herein relates to an organic electroluminescence device and a heterocyclic compound for an organic electroluminescence device.

2. Description of the Related Art

As an image display device, an organic electroluminescence display device has been actively developed. An organic electroluminescence display device is different from a liquid crystal display device and the like in that it is a so-called self-luminescence display device, which realizes display by recombining holes and electrons injected respectively from a first electrode and a second electrode in a light emitting layer to emit light from a light emitting material, which is an organic compound included in the light emitting layer.

As an organic electroluminescence device, for example, an organic device including a first electrode, a hole transport layer disposed on the first electrode, a light emitting layer disposed on the hole transport layer, an electron transport layer disposed on the light emitting layer, and a second electrode disposed on the electron transport layer is known. From the first electrode, holes are injected, and the injected holes move through the hole transport layer to be injected to the light emitting layer. From the second electrode, electrons are injected, and the injected electrons move through the electron transport layer to be injected to the light emitting layer. The holes and the electrons, both injected to the light emitting layer, are recombined to generate excitons in the light emitting layer. An organic electroluminescence device emits light utilizing light generated when the excitons fall to a ground state again. Furthermore, an organic electroluminescence device is not limited to the configuration described above, and various suitable modifications thereof may be made.

SUMMARY

Aspects according to one or more embodiments of the present disclosure are directed toward an organic electroluminescence device and a heterocyclic compound for an organic electroluminescence device, and more particularly, to an organic electroluminescence device radiating thermally activated delayed fluorescence and a heterocyclic compound utilized therefor.

According to an embodiment of the inventive concept, an organic electroluminescence device includes a first electrode, a hole transport region on the first electrode, a light emitting layer on the hole transport region, an electron transport region on the light emitting layer, and a second electrode on the electron transport region, wherein the light emitting layer includes a heterocyclic compound represented by Formula 1 below.

$$D_1\text{-}A\text{-}D_2 \qquad \text{Formula 1}$$

In Formula 1, $D_1$ and $D_2$ are each independently represented by Formula 2 below, and A is represented by any one of Formulas 3-1 to 3-3 below.

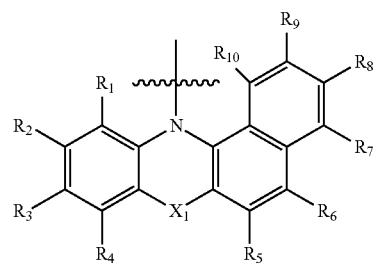

Formula 2

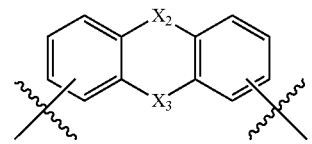

Formula 3-1

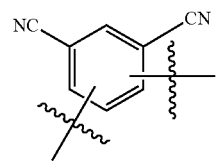

Formula 3-2

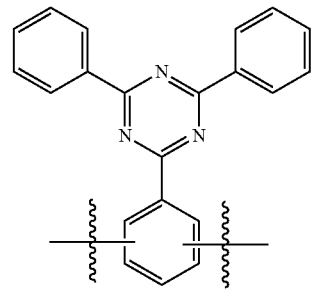

Formula 3-3

In Formula 2, $X_1$ is S, O, or $CY_1Y_2$, and $R_1$ to $R_{10}$, $Y_1$ and $Y_2$ are each independently a hydrogen atom, a deuterium atom, a substituted or unsubstituted alkyl group having 1 to 10 carbon atoms, or a substituted or unsubstituted aryl group having 6 to 30 ring-forming carbon atoms.

In Formula 3-1, $X_2$ is $SO_2$ or O, $X_3$ is a direct linkage or $CY_3Y_4$, and $Y_3$ and $Y_4$ are each independently a hydrogen atom, a deuterium atom, a substituted or unsubstituted alkyl group having 1 to 10 carbon atoms, or a substituted or unsubstituted aryl group having 6 to 30 ring-forming carbon atoms.

In an embodiment, the light emitting layer may include a host and a dopant, and the dopant may include a heterocyclic compound represented by Formula 1.

In an embodiment, the dopant may be a thermally activated delayed fluorescence dopant.

In an embodiment of the inventive concept, a heterocyclic compound for an electroluminescence device is provided, which is represented by Formula 1 described above.

In an embodiment, in Formula 1, A may be represented by any one of Formulas 4-1 to 4.3 below.

Formula 4-1

Formula 4-2

Formula 4-3

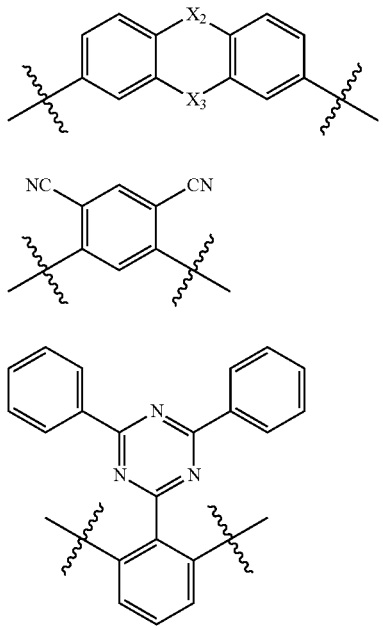

In Formula 4-1, $X_2$ and $X_3$ are the same as described above.

In an embodiment, A represented by Formula 3-1 may be represented by any one of Formulas 3-1-1 to 3-1-3 below.

Formula 3-1-1

Formula 3-1-2

Formula 3-1-3

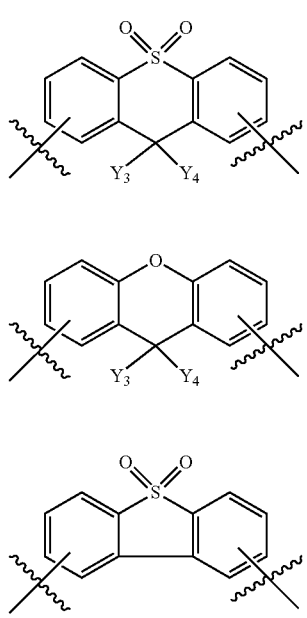

In Formulas 3-1-1 and 3-1-2, $Y_3$ and $Y_4$ are the same as described above.

In an embodiment, A represented by Formula 3-1 may be represented by any one of Formulas 3-1-4 to 3-1-6 below.

Formula 3-1-4

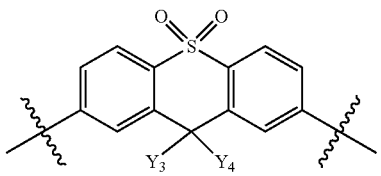

Formula 3-1-5

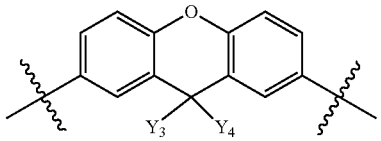

Formula 3-1-6

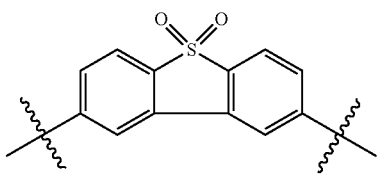

In Formulas 3-1-4 and 3-1-5, $Y_3$ and $Y_4$ are the same as described above.

In an embodiment, in at least one of $D_1$ and $D_2$, $X_1$ may be $CY_1Y_2$, $Y_1$ and $Y_2$ may be same as defined above, and A may be represented by Formula 3-3.

In an embodiment, in at least one of $D_1$ and $D_2$, $X_1$ may be $CY_1Y_2$, $Y_1$ and $Y_2$ may be each independently a substituted or unsubstituted alkyl group having 1 to 5 carbon atoms, and A may be represented by Formula 3-3.

In an embodiment, in Formula 1, $D_1$ and $D_2$ may be the same.

In an embodiment, in Formula 1, $D_1$ and $D_2$ may be different from each other.

BRIEF DESCRIPTION OF THE DRAWINGS

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
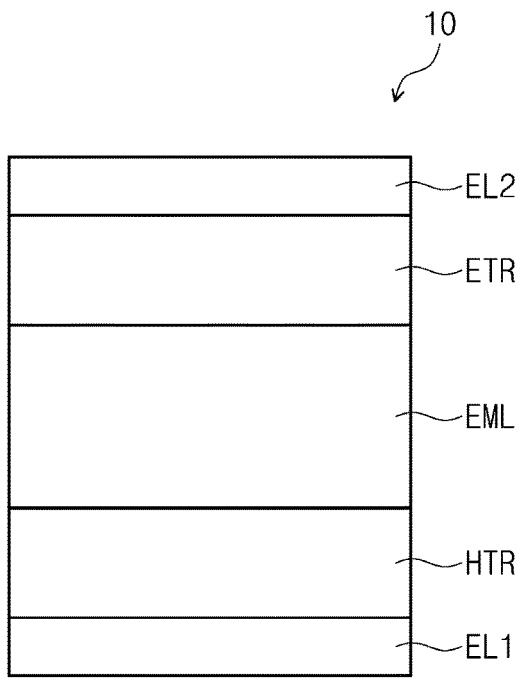
FIG. 1 is a cross-sectional view schematically illustrating an organic electroluminescence device according to an embodiment of the inventive concept.

Aspects, features, and enhancements of the inventive concept described above may be understood easily with reference to the exemplary embodiments and the accompanying drawings. The inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art.

In describing each drawing, similar reference numerals may be used for similar elements. Also, in the accompanying drawings, the dimensions of structures may be exaggerated for the clarity of the inventive concept. It will be understood that, although the terms "first," "second," etc., may be used herein to describe various elements, these elements should not be limited by these terms. These terms are used only to distinguish one element from another. For example, a first element could be termed a second element, and similarly, a second element could be termed a first element without departing from the scope of the inventive concept. Terms of a singular form may include terms of a plural form unless the context clearly indicates otherwise. As used herein, the singular forms, "a" and "an" are intended to include the plural forms as well, unless the context clearly indicates otherwise.

In this disclosure, terms "comprise," "include" and "have" are intended to designate the presence of features, numbers, steps, operations, elements, parts, or combinations thereof described in the specifications of the inventive concept, but not to exclude the possibility of the presence or the addition of one or more other features, numbers, steps, operations, elements, parts, or combinations thereof. It will also be understood that when a portion of a structure, such as a layer, a film, a region, or a plate, is referred to as being "on," or "over" another portion, it can be "directly on" the other portion, or one or more intervening portions may also be present. Similarly, it will be understood that when a portion of a structure, such as a layer, a film, a region, or a plate, is referred to as being "under" another portion, it can be "directly under", or one or more intervening portions may also be present.

The terminology used herein is for the purpose of describing particular embodiments only and is not intended to be limiting of the scope of the invention. Expressions such as "at least one of," when preceding a list of elements, modify the entire list of elements and do not modify the individual elements of the list. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Figure 2:
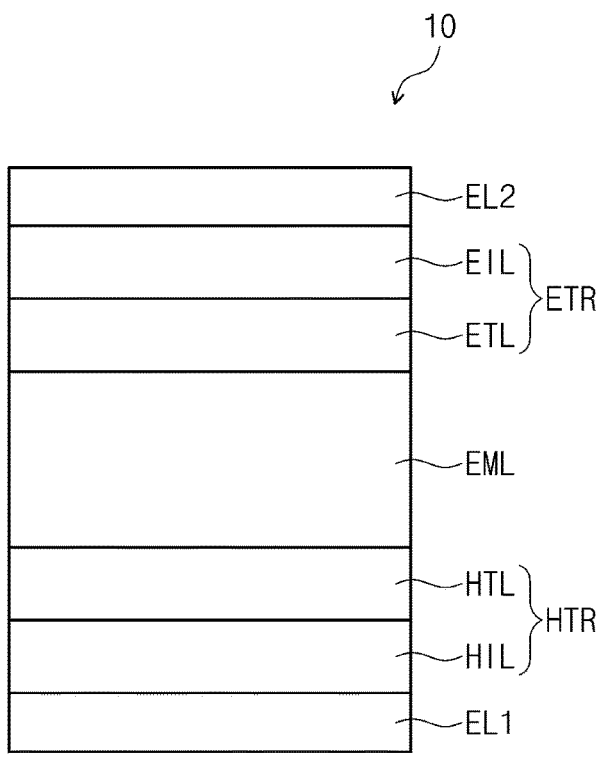
FIG. 2 is a cross-sectional view schematically illustrating an organic electroluminescence device according to an embodiment of the inventive concept.

Referring to FIGS. 1 and 2, an organic electroluminescence device according to an embodiment of the inventive concept will be described in more detail.

FIG. 1 is a cross-sectional view schematically illustrating an organic electroluminescence device according to an embodiment of the inventive concept. FIG. 2 is a cross-sectional view schematically illustrating an organic electroluminescence device according to an embodiment of the inventive concept.

Referring to FIGS. 1 and 2, an organic electroluminescence device 10 according to an embodiment of the inventive concept includes a first electrode EL1, a hole transport region HTR, a light emitting layer EML, an electron transport region ETR, and a second electrode EL2.

The first electrode EL1 and the second electrode EL2 are disposed to face each other, and between the first electrode EL1 and the second electrode EL2, a plurality of organic layers may be disposed. In other words, the first and second electrodes EL1 and EL2 may be located on opposite sides with respect to the plurality of organic layers. The plurality of organic layers may include the hole transport region HTR, the light emitting layer EML, and the electron transport region ETR.

The first electrode EL1 has conductivity. The first electrode EL1 may be a pixel electrode or a positive electrode. The first electrode EL1 may be a transmissive electrode, a transflective electrode, or a reflective electrode. When the first electrode EL1 is a transmissive electrode, the first electrode EL1 may include a transparent metal oxide, for example, indium tin oxide (ITO), indium zinc oxide (IZO), zinc oxide (ZnO), indium tin zinc oxide (ITZO), and/or the like. When the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, or a compound or a mixture thereof (for example, a mixture of Ag and Mg). The first electrode EL1 may have a multilayer structure including a reflective film or a transflective film, each formed of the above described materials, and a transparent conductive film formed of indium tin oxide (ITO), indium zinc oxide (IZO), zinc oxide (ZnO), indium tin zinc oxide (ITZO), and/or the like. For example, the first electrode EL1 may have a three-layer structure of ITO/Ag/ITO, or a three-layer structure of Ag/ITO/Ag, but the inventive concept is not limited thereto.

The thickness of the first electrode EL1 may be about 1000 Å to about 10000 Å, for example, about 1000 Å to about 3000 Å.

The hole transport region HTR is provided on the first electrode EL1. The hole transport region HTR may include at least one of a hole injection layer HIL, a hole transport layer HTL, a hole buffer layer, or an electron blocking layer. The thickness of the hole transport region HTR may be, for example, about 1000 Å to about 1500 Å.

The hole transport region HTR may have a single layer structure (i.e., having a single layer) formed of a single material, a single layer structure (i.e., having a single layer) formed of a plurality of different materials, or a multilayer structure having a plurality of layers formed of a plurality of different materials.

For example, the hole transport region HTR may have a single layer structure (i.e., having a single layer) of the hole injection layer HIL or the hole transport layer HTL, or have a single layer structure (i.e., having a single layer) formed of a hole injection material and a hole transport material. Also, the hole transport region HTR may have a single layer structure (i.e., having a single layer) formed of a plurality of different materials, or have a structure of the hole injection layer HIL/the hole transport layer HTL, the hole injection layer HIL/the hole transport layer HTL/the hole buffer layer, the hole injection layer HIL/the hole buffer layer, the hole transport layer HTL/the hole buffer layer, or the hole injection layer HIL/the hole transport layer HTL/the electron blocking layer EBL, sequentially laminated on the first electrode EL1 (e.g., in the stated order), but the inventive concept is not limited thereto.

The hole transport region HTR may be formed by various suitable methods such as vacuum deposition, spin coating, casting, Langmuir-Blodgett (LB), inkjet printing, laser printing, and/or laser induced thermal imaging (LITI).

The hole injection layer HIL may include, for example, a phthalocyanine compound (such as copper phthalocyanine); N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4'4"-Tris(N,N-diphenylamino)triphenylamine (TDATA), 4,4',4''-tris{N,-(2-naphthyl)-N-phenylamino}-triphenylamine (2-TNATA), Poly(3,4-ethylenedioxythiophene)/Poly(4-styrenesulfonate) (PEDOT/PSS), Polyaniline/Dodecylbenzenesulfonic acid (PANI/DBSA), Polyaniline/Camphor sulfonic acid PANI/CSA), (Polyaniline)/Poly(4-styrenesulfonate) (PANI/PSS), N,N'-di(naphthalene-1-yl)-N,N'-diplienyl-benzidine (NPD), triphenylamine-containing polyether ketone (TPAPEK), 4-Isopropyl-4'-methyldiphenyliodonium Tetrakis(pentafluorophenyl)borate], dipyrazino [2,3-f: 2',3'-h] quinoxaline-2,3,6,7,10,11-hexacarbonitrile (HAT-CN), and/or the like.

The hole transport layer HTL may include, for example, a carbazole-based derivative (such as N-phenylcarbazole or polyvinylcarbazole), a fluorine-based derivative, a triphenylamine-based derivative (such as N,N'-bis(3-methylphenyl)-N,N'-diphenyl-[1,1-biphenyl]-4,4'-diamine (TPD) or 4,4',4''-tris(N-carbazolyl)triphenylamine (TCTA)), N,N'-di(naphthalene-1-yl)-N,N'-diplienyl-benzidine (NPD), 4,4'-Cyclohexylidene bis[N,N-bis(4-methylphenyl)benzenamine] (TAPC), 4,4'-Bis[N,N'-(3-tolyl)amino]-3,3'-dimethylbiphenyl (HMTPD), and/or the like.

The thickness of the hole transport region HTR may be about 100 Å to about 10000 Å, for example, about 100 Å to about 1000 Å. When the hole transport region HTR includes both the hole injection layer HIL and the hole transport layer HTL, the thickness of the hole injection layer HIL may be about 100 Å to about 10000 Å, for example, about 100 Å to about 1000 Å, and the thickness of the hole transport layer HTL may be about 30 Å to about 1000 Å. When the thicknesses of the hole transport region HTR, the hole injection layer HIL, and the hole transport layer HTL satisfy the above-described ranges, satisfactory hole transport properties may be obtained without a substantial increase in driving voltage.

The hole transport region HTR may further include a charge generating material to improve the conductivity in addition to the above-mentioned materials. The charge generating material may be uniformly or non-uniformly dispersed in the hole transport region HTR. The charge generating material may be, for example, a p-dopant. The p-dopant may be one of a quinone derivative, a metal oxide, or a compound containing a cyano group, but the inventive concept is not limited thereto. For example, non-limiting examples of the p-dopant may include a quinone derivative (such as tetracyanoquinodimethane (TCNQ) or 2,3,5,6-tetrafluoro-tetracyanoquinodimethane (F4-TCNQ)), and a metal oxide (such as a tungsten oxide or a molybdenum oxide), but the inventive concept is not limited thereto.

As described above, the hole transport region HTR may further include at least one of a hole buffer layer and an electron blocking layer in addition to the hole injection layer HIL and the hole transport layer HTL. The hole buffer layer may increase light emission efficiency by compensating for a resonance distance according to the wavelength of light emitted from the light emitting layer EML. As for materials which may be included in the hole buffer layer, materials which may be included in the hole transport region HTR may be utilized. The electron blocking layer is a layer serving to prevent or reduce electron injection from the electron transporting region ETR to the hole transporting region HTR.

The light emitting layer EML is provided on the hole transport region HTR. The thickness of the light emitting layer EML may be, for example, about 100 Å to about 1000 Å, or about 100 Å to about 300 Å. The light emitting layer EML may have a single layer structure (i.e., having a single layer) formed of a single material, a single layer structure (i.e., having a single layer) formed of a plurality of different materials, or a multilayer structure having a plurality of layers formed of a plurality of different materials.

A more detailed description on the material of the light emitting layer EML, the light emission wavelength, and the like will be provided later.

The electron transport region ETR is provided on the light emitting layer EML. The electron transport region ETR may include at least one of a hole blocking layer, an electron transport layer ETL, or an electron injection layer EIL, but the inventive concept is not limited thereto.

The electron transport region ETR may have a single layer structure (i.e., having a single layer) formed of a single material, a single layer structure (i.e., having a single layer) formed of a plurality of different materials, or a multilayer structure having a plurality of layers formed of a plurality of different materials.

For example, the electron transport region ETR may have a single layer structure (i.e., having a single layer) of the electron injection layer EIL or the electron transport layer ETL, or a single layer structure (i.e., having a single layer) formed of an electron injection material and an electron transport material. Also, the electron transport region ETR may have a single layer structure (i.e., having a single layer) formed of a plurality of different materials, or have a structure of the electron transport layer ETL/the electron injection layer EIL, a hole blocking layer/the electron transport layer ETL/the electron injection layer EIL, sequentially laminated on the first electrode EL1 (e.g., in the stated order), but the inventive concept is not limited thereto. The thickness of the electron transport region ETR may be, for example, about 1000 Å to about 1500 Å.

The electron transport region ETR may be formed by various suitable methods such as vacuum deposition, spin coating, casting, Langmuir-Blodgett (LB), inkjet printing, laser printing, and/or laser induced thermal imaging (LITI).

When the electron transport region ETR includes the electron transport layer ETL, the electron transport region ETR may include an anthracene-based compound, but the inventive concept is not limited thereto. The electron transport region ETR may include Tris(8-hydroxyquinolinato) aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-Tri(1-phenyl-1H-benzo[d]imidazol-2-yl)phenyl (TPBi), 2,9-Dimethyl-4,7-diphenyl-1,10-phenanthroline (BCP), 4,7-Diphenyl-1,10-phenanthroline (Bphen), 3-(4-Biphenylyl)-4-phenyl-5-tert-butylphenyl-1,2,4-triazole (TAZ), 4-(Naphthalen-1-yl)-3,5-diphenyl-4H-1,2,4-triazole (NTAZ), tBu-PBD(2-(4-Biphenylyl)-5-(4-tert-butylphenyl)-1,3,4-oxadiazole), Bis(2-methyl-8-quinolinolato-N1,O8)-(1,1'-Biphenyl-4-olato)aluminum (BAlq), berylliumbis(benzoquinolin-10-olate (Bebq$_2$), 9,10-di(naphthalene-2-yl)anthracene (ADN), and/or a compound thereof. The thickness of the electron transport layer ETL may be about 100 Å to about 1000 Å, for example, about 150 Å to about 500 Å. When the thickness of the electron transport layer ETL satisfies the above-described ranges, satisfactory electron transport properties may be obtained without a substantial increase in driving voltage.

When the electron transport region ETR includes the electron injection layer EIL, the electron transporting region ETR (e.g., the electron injection layer) may include a lanthanum group metal (such as LiF, Lithium quinolate (LiQ), Li$_2$O, BaO, NaCl, CsF, or Yb), or a halogenated metal (such as RbCl or RbI), but the inventive concept is not limited thereto. The electron injection layer EIL may include a mixture of an electron transport material and an insulating organo metal salt. The organo metal salt may be a material having an energy band gap of about 4 eV or greater. For example, the organo metal salt may include metal acetate, metal benzoate, metal acetoacetate, metal acetylacetonate, or metal stearate. The thickness of the electron injection layer EIL may be about 1 Å to about 100 Å, or about 3 Å to about 90 Å. When the thickness of the electron injection layer EIL satisfies the above-described ranges, satisfactory electron injection properties may be obtained without a substantial increase in driving voltage.

The electron transport region ETR may include a hole blocking layer as described above. The hole blocking layer may include, for example, at least one of 2,9-dimethyl-4,7-diphenyl-1,10-phenanthroline (BCP) and 4,7-diphenyl-1,10-phenanthroline (Bphen), but the inventive concept is not limited thereto.

The second electrode EL2 is provided on the electron transport region ETR. The second electrode EL2 may be a common electrode or a negative electrode. The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), and/or the like.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, or a compound or a mixture thereof (for example, a mixture of Ag and Mg). Also, the second electrode EL2 may be of a multilayer structure including a reflective film or a transflective film, each formed of the above described materials, and a transparent conductive film formed of indium tin oxide (ITO), indium zinc oxide (IZO), zinc oxide (ZnO), indium tin zinc oxide (ITZO), and/or the like.

Although not illustrated, the second electrode EL2 may be connected to an auxiliary electrode. When the second electrode EL2 is connected to the auxiliary electrode, the resistance of the second electrode EL2 may be reduced.

In the organic electroluminescence device 10, when voltage is applied to the first electrode EL1 and the second electrode EL2 respectively, holes injected from the first electrode EL1 move to the light emitting layer EML through the hole transport layer HTR, and electrons injected from the second electrode EL2 move to the light emitting layer EML through the electron transport layer ETR. The holes and the electrons are recombined in the light emitting layer EML to generate excitons, and light is emitted when the excitons fall from an excited state to a ground state.

When the organic electroluminescence device 10 is a top emission device, the first electrode EL1 may be a reflective electrode, and the second electrode EL1 may be a transmissive electrode or a transflective electrode. When the organic electroluminescence device 10 is a bottom emission device, the first electrode EL1 may be a transmissive electrode or a transflective electrode, and the second electrode EL2 may be a reflective electrode.

An embodiment of the inventive concept provides a heterocyclic compound for an organic electroluminescence device. The light emitting layer EML includes the heterocyclic compound according to an embodiment of the inventive concept. That is, the heterocyclic compound according to an embodiment of the inventive concept may be utilized as a material for the light emitting layer EML of the organic electroluminescence device 10.

Hereinafter, the heterocyclic compound according to an embodiment of the inventive concept will be described in more detail.

In this disclosure,

refers to a portion to be connected.

In this disclosure, the term "substituted or unsubstituted" may refer to an unsubstituted functional group, or a functional group substituted with one or more substituents selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a hetero ring group. In addition, each of the substituents illustrated above may be substituted or unsubstituted. For example, a biphenyl group may be interpreted as an aryl group, and may be interpreted as a phenyl group substituted with a phenyl group. The term "hetero ring group" may refer to an aliphatic hetero ring and/or an aromatic hetero ring (i.e., a heteroaryl group).

For example, in this disclosure, the term "substituted or unsubstituted" may refer to an unsubstituted functional group, or a functional group substituted with one or more substituents selected from the group consisting of a deuterium atom, a halogen atom, an alkyl group, and an aryl group.

In this disclosure, examples of the halogen atom may include a fluorine atom, a chlorine atom, a bromine atom, or an iodine atom.

In this disclosure, the alkyl group may be linear, branched or cyclic. The number of carbon atoms of the alkyl group may be 1 to 30, 1 to 20, 1 to 10, or 1 to 6. Examples of the alkyl group may include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantly group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldodecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-heneicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, and/or the like, but the inventive concept is not limited thereto.

In this disclosure, the alkenyl group may be linear or branched. The number of carbon atoms is not particularly limited, and may be 2 to 30, 2 to 20, or 2 to 10. Examples of the alkenyl group may include, a vinyl group, a 1-butenyl group, a 1-pentenyl group, a 1,3-butadienylaryl group, a styrenyl group, a styryl vinyl group, and the like, but the inventive concept is not limited thereto.

In this disclosure, the term "aryl group" may refer to any functional group or substituent derived from an aromatic hydrocarbon ring. The aryl group may be a monocyclic aryl group or a polycyclic aryl group. The number of ring-forming carbon atoms of the aryl group may be 6 to 60, 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinphenyl group, a sexiphenyl group, a biphenylene group, a triphenylene group, a pyrenyl group, a benzofluoranthenyl group, a chrysenyl group, and/or the like, but the inventive concept is not limited thereto.

In this disclosure, the fluorenyl group may be substituted, and two substituents may be bonded to each other to form a spiro structure. Examples of a substituted fluorenyl group are as follows. However, the inventive concept is not limited thereto.

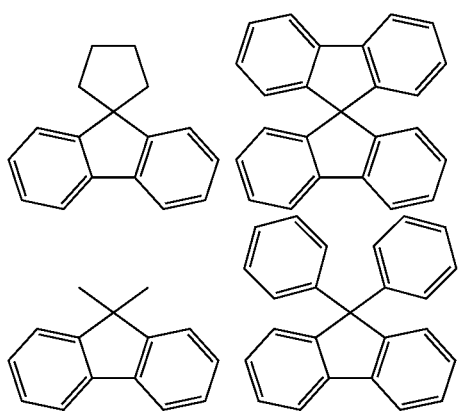

In this disclosure, the heteroaryl group may be a heteroaryl group including one or more of O, N, P, Si and S as a heteroatom.

In this disclosure, the term "silyl group" may refer to an alkylsilyl group and/or an arylsilyl group. Examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and/or the like, but the inventive concept is not limited thereto.

In this disclosure, the term "boron group" may refer to an alkyl boron group and/or an aryl boron group. Examples of the boron group may include a trimethylboron group, a triethylboron group, a t-butyldimethylboron group, a triphenylboron group, a diphenylboron group, a phenylboron group, and/or the like, but the inventive concept is not limited thereto.

In this disclosure, the number of carbon atoms of the amino group is not particularly limited, and may be 1 to 30.

The amino group may include an alkylamino group and/or an arylamino group. Examples of the amino group may include a methylamino group, a dimethylamino group, a phenylamino group, a diphenylamino group, a naphthylamino group, a 9-methyl-anthracenylamino group, a triphenylamino group, and/or the like, but the inventive concept is not limited thereto.

In this disclosure, the phosphine oxide group may be substituted with, for example, at least one of an alkyl group and an aryl group. Examples of the phosphine oxide group may include a phenylphosphine oxide group, a diphenylphosphine oxide group, and/or the like, but the inventive concept is not limited thereto.

In this disclosure, the phosphine sulfide group may be substituted with at least one of an alkyl group and an aryl group.

In this disclosure, a "direct linkage" may refer to a single bond.

The heterocyclic compound according to an embodiment of the inventive concept may be represented by Formula 1 below.

In Formula 1, $D_1$ and $D_2$ are each independently an electron-donating group, and A is an electron-accepting group. The heterocyclic compound according to an embodiment of the inventive concept includes an electron-donating group and an electron-accepting group separated in one molecule, and includes two electron-donating groups.

In Formula 1, $D_1$ and $D_2$ are each independently represented by Formula 2 below.

Formula 2

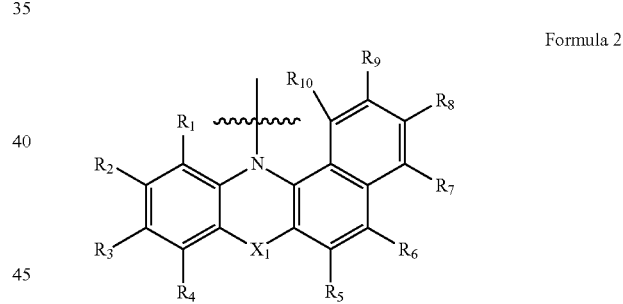

In Formula 2, $X_1$ is S, O, or $CY_1Y_2$, and $R_1$ to $R_{10}$, $Y_1$ and $Y_2$ are each independently a hydrogen atom, a deuterium atom, a substituted or unsubstituted alkyl group having 1 to 10 carbon atoms, or a substituted or unsubstituted aryl group having 6 to 30 ring-forming carbon atoms.

$D_1$ and $D_2$ may be the same. However, the embodiment of the inventive concept is not limited thereto. $D_1$ and $D_2$ may be different from each other.

In Formula 1, A is represented by any one of Formulas 3-1 to 3-3 below.

Formula 3-1

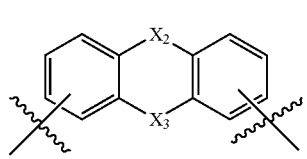

-continued

Formula 3-2

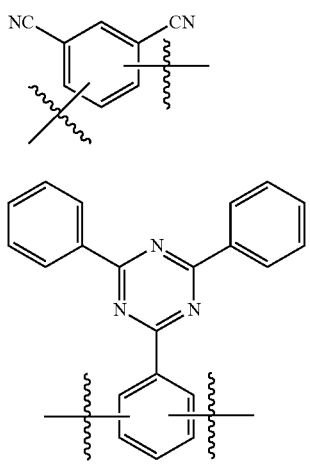

Formula 3-3

In Formula 3-1, $X_2$ is $SO_2$ or O, $X_3$ is a direct linkage or $CY_3Y_4$, and $Y_3$ and $Y_4$ are each independently a hydrogen atom, a deuterium atom, a substituted or unsubstituted alkyl group having 1 to 10 carbon atoms, or a substituted or unsubstituted aryl group having 6 to 30 ring-forming carbon atoms.

When $X_3$ is a direct linkage, the ring containing $X_2$ is a 5-membered ring.

Each of Formulas 3-1 to 3-3 may be further substituted additionally, and a substituent may be at least one selected from a deuterium, an alkyl group, or an aryl group.

A represented by Formula 3-1 may be represented by, for example, Formula 4-1 below.

Formula 4-1

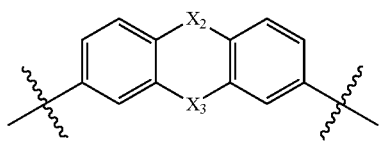

In Formula 4-1, $X_2$ and $X_3$ are the same as defined in Formula 3-1.

A represented by Formula 3-1 may be represented by any one of Formulas 3-1-1 to 3-1-3 below.

Formula 3-1-1

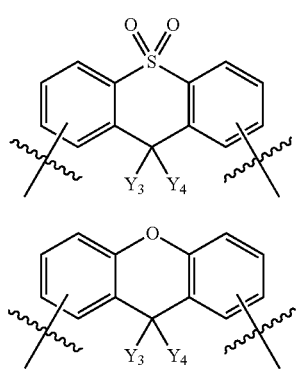

Formula 3-1-2

Forula 3-1-3

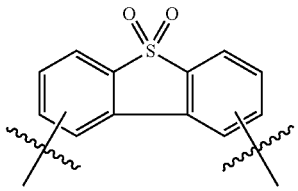

In Formula 3-1-1 and 3-1-2, $Y_3$ and $Y_4$ are the same as defined in Formula 3-1.

$Y_3$ and $Y_4$ may be each independently a substituted or unsubstituted alkyl group having 1 to 10 carbon atoms, or a substituted or unsubstituted aryl group having 6 to 30 ring-forming carbon atoms.

$Y_3$ and $Y_4$ may be each independently a substituted or unsubstituted methyl group, or a substituted or unsubstituted phenyl group. However, the inventive concept is not limited thereto. For example, $Y_3$ and $Y_4$ may be each independently a substituted or unsubstituted methyl group.

For example, A represented by Formula 3-1-1 may be represented by Formula 3-1-4 below.

Formula 3-1-4

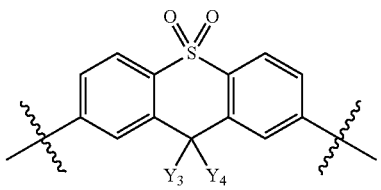

In Formula 3-1-4, $Y_3$ and $Y_4$ may be the same as defined in Formula 3-1.

A represented by Formula 3-1-2 may be represented by, for example, Formula 3-1-5 below.

Formula 3-1-5

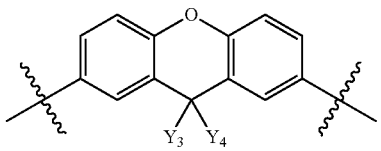

In Formula 3-1-5, $Y_3$ and $Y_4$ may be the same as defined in Formula 3-1.

A represented by Formula 3-1-3 may be represented by, for example, Formula 3-1-6 below.

Formula 3-1-6

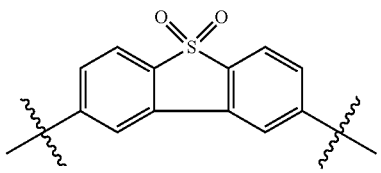

In one embodiment, A represented by Formula 3-2 is (e.g., preferably) represented by Formula 4-2 below. However, the inventive concept is not limited thereto.

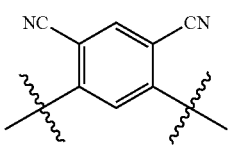

Formula 4-2

In one embodiment, A represented by Formula 3-3 is (e.g., preferably) represented by Formula 4-3 below. However, the inventive concept is not limited thereto.

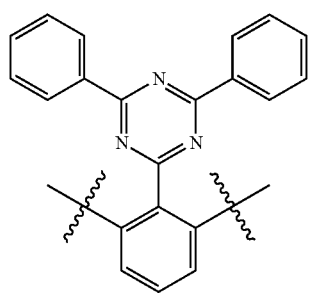

Formula 4-3

In an embodiment, in at least one of $D_1$ and $D_2$, $X_1$ in Formula 2 may be $CY_1Y_2$, and A may be represented by Formula 3-3. $Y_1$ and $Y_2$ are the same as defined in Formula 2, and for example, may be a substituted or unsubstituted alkyl group having 1 to 5 carbon atoms, or a substituted or unsubstituted aryl group having 6 to 20 carbon atoms. For example, $Y_1$ and $Y_2$ may be each independently a substituted or unsubstituted methyl group, or a substituted or unsubstituted phenyl group. However, the inventive concept is not limited thereto.

In Formula 2, $X_1$ may be $CY_1Y_2$, and $Y_1$ and $Y_2$ may be each independently a substituted or unsubstituted alkyl group having 1 to 10 carbon atoms, or a substituted or unsubstituted aryl group having 6 to 30 ring-forming carbon atoms. For example, $Y_1$ and $Y_2$ may be each independently a substituted or unsubstituted methyl group, or a substituted or unsubstituted phenyl group. However, the inventive concept is not limited thereto.

In Formula 2, $X_1$ may be O or S.

In Formula 2, $R_1$ to $R_{10}$ may be each independently a hydrogen atom. However, the inventive concept is not limited thereto. A substituent may be introduced to be properly applied to an organic electroluminescence device. For example, at least one of $R_1$ to $R_{10}$ may be a substituent other than a hydrogen atom, and may be a deuterium, a methyl group, a butyl group, or a phenyl group. At least one of $R_1$ to $R_{10}$ may be a methyl group or a t-butyl group, but the inventive concept is not limited thereto.

The heterocyclic compound represented by Formula 1 according to an embodiment of the inventive concept may be any one selected from the compounds represented by Compound Group 1 below. However, the inventive concept is not limited thereto. In the compound structure below, Ph represents a phenyl group. Compound Group 1

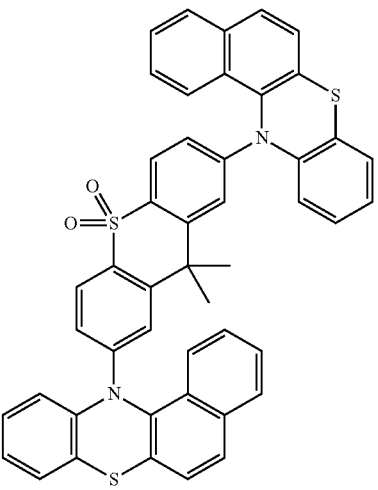

TD-1

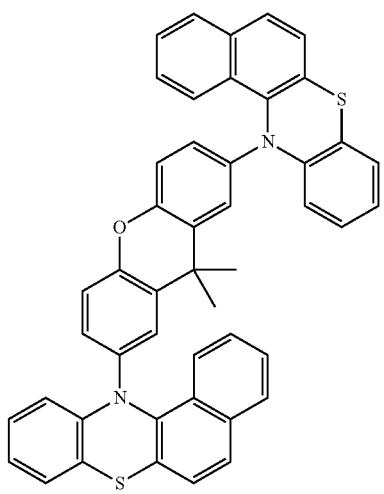

TD-2

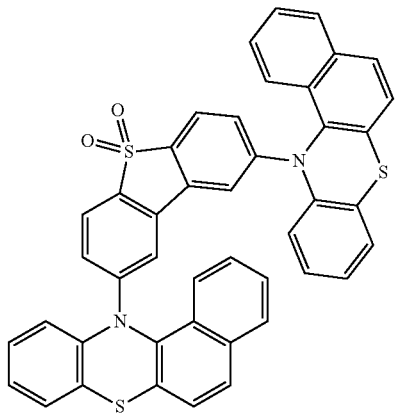

TD-3

TD-4
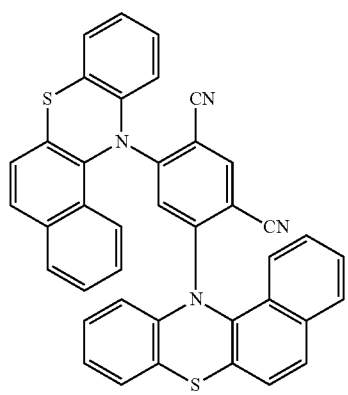
TD-5
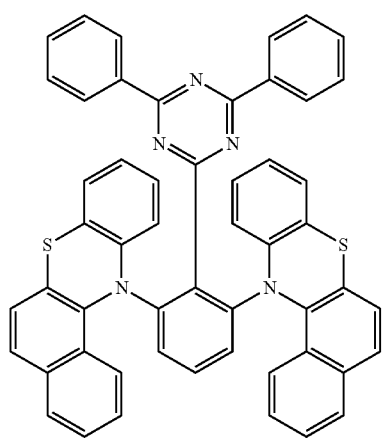
TD-6
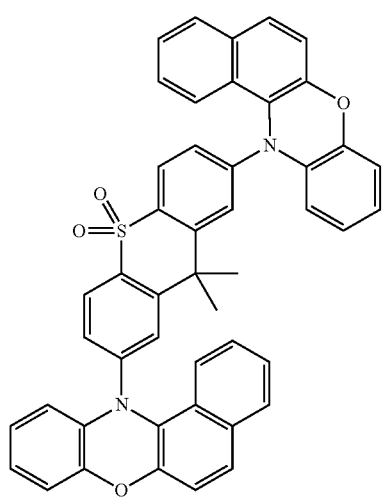
TD-7
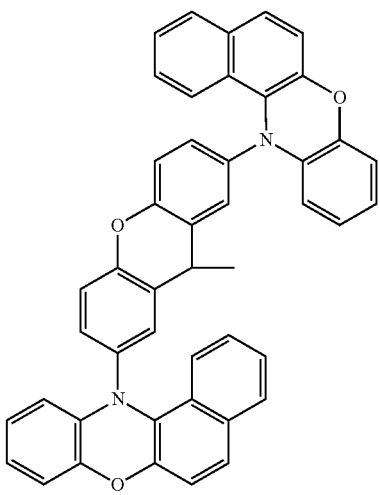
TD-8
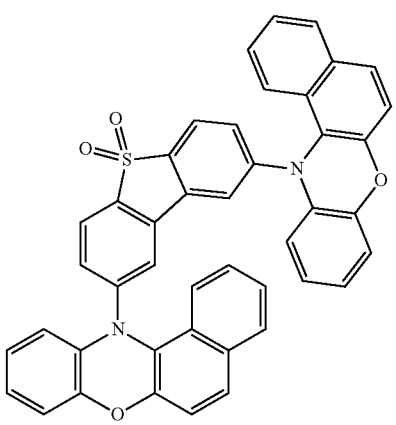
TD-9
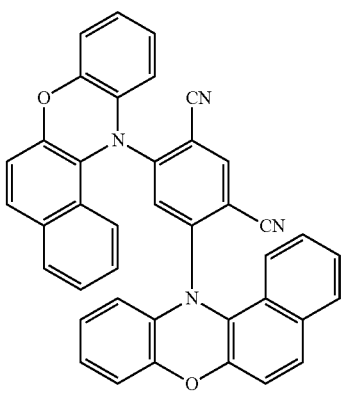

TD-10
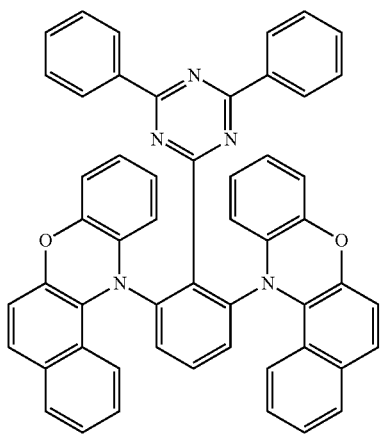
TD-11
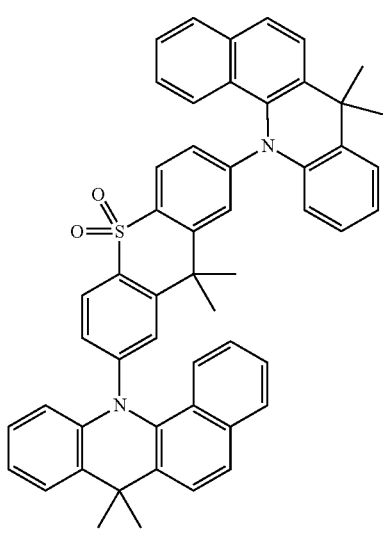
TD-12
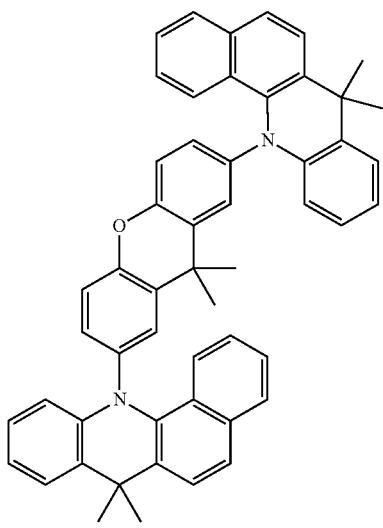
TD-13
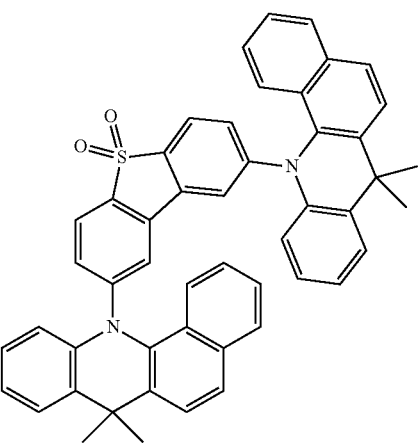
TD-14
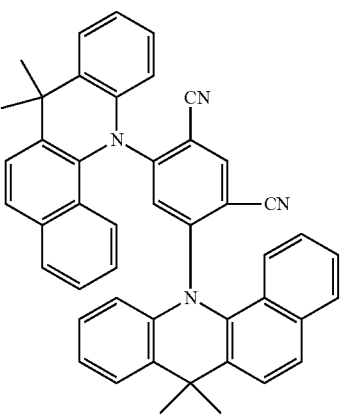
TD-15
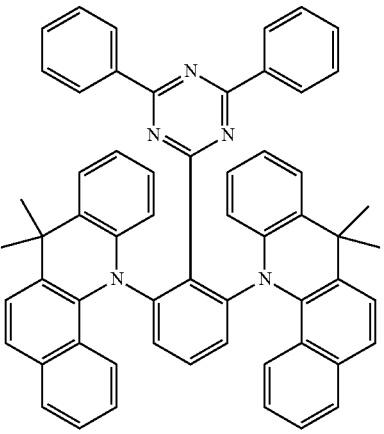

TD-16
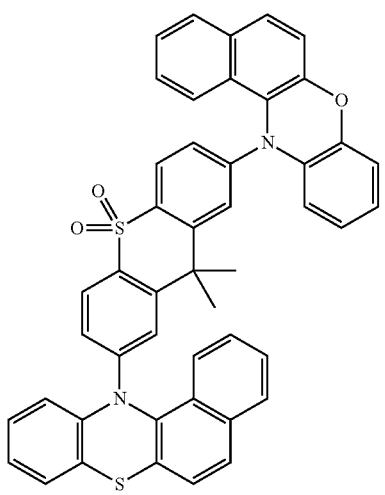
TD-17
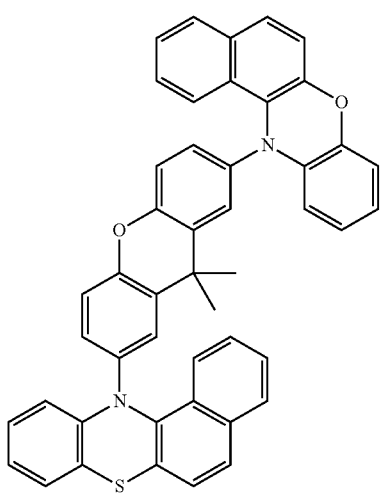
TD-18
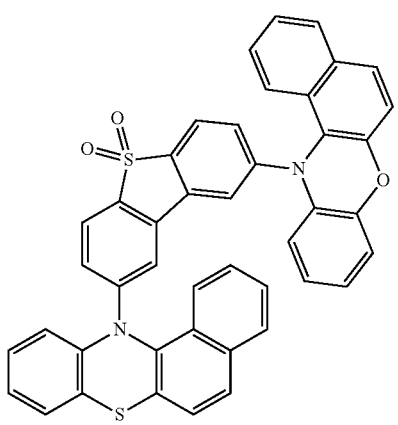
TD-19
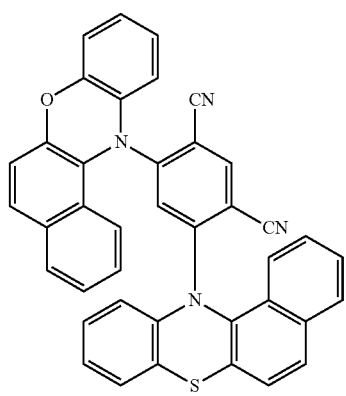
TD-20
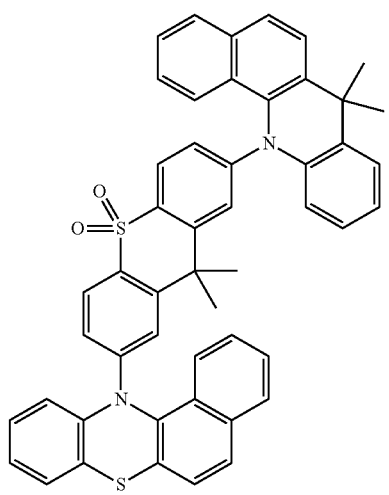
TD-21
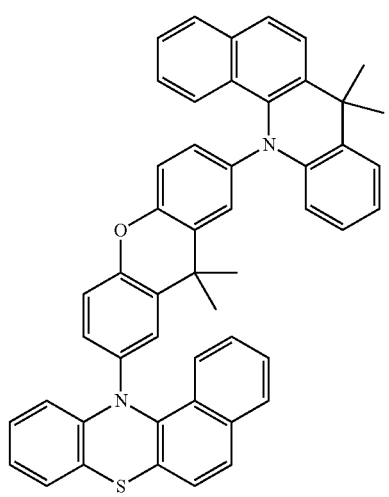

TD-22
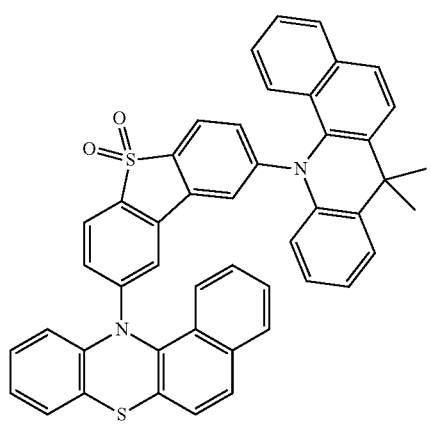
TD-25
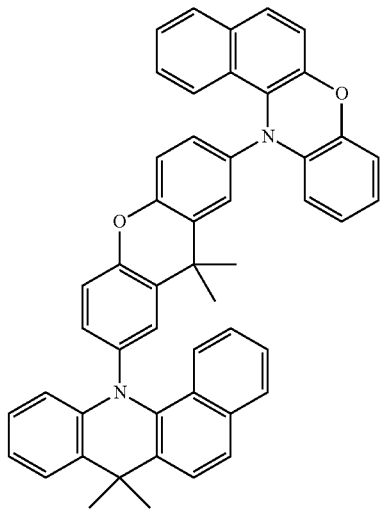
TD-23
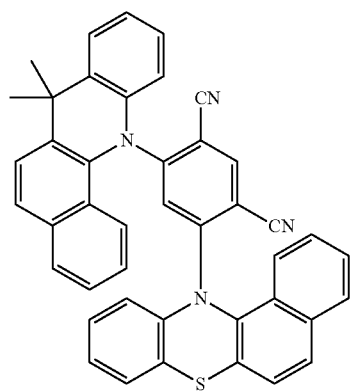
TD-26
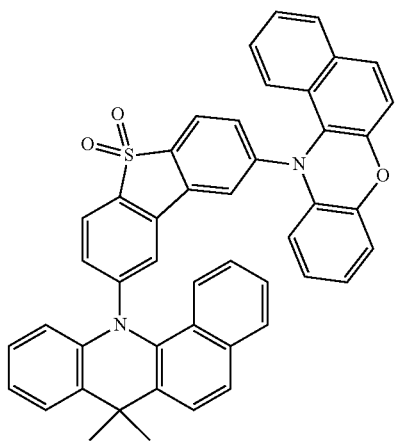
TD-24
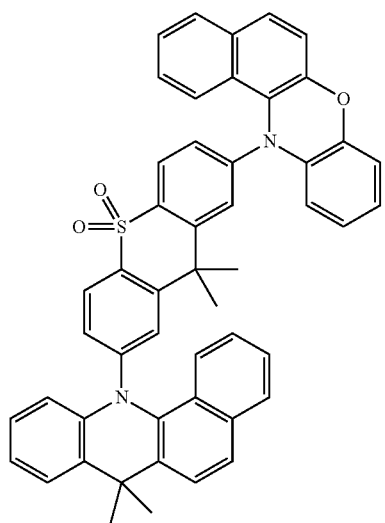
TD-27
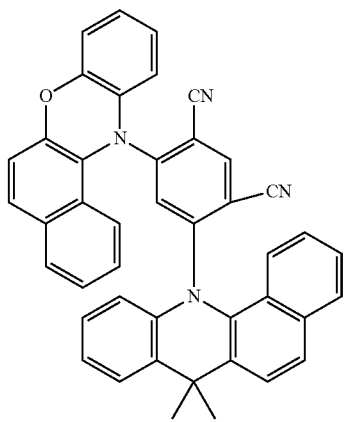

TD-28
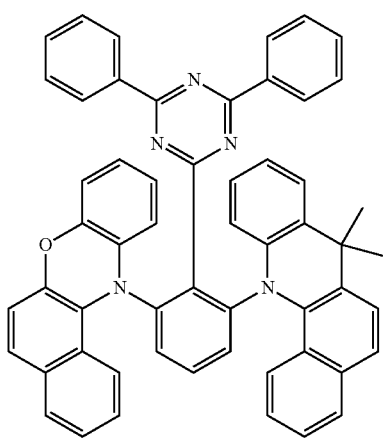
TD-29
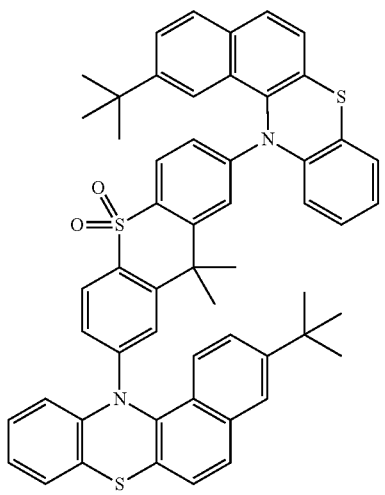
TD-30
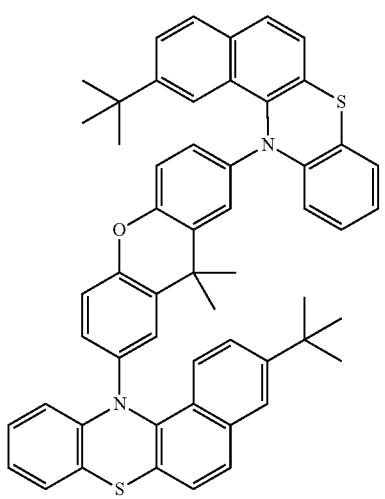
TD-31
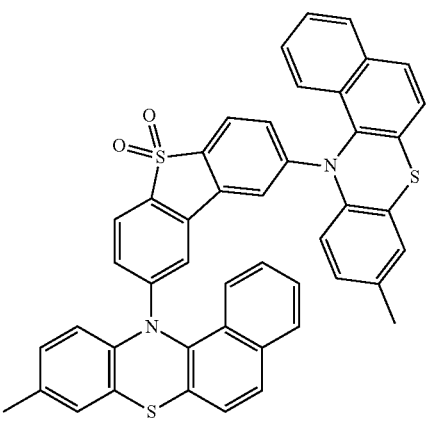
TD-32
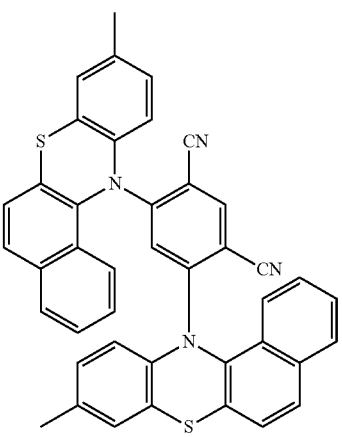
TD-33
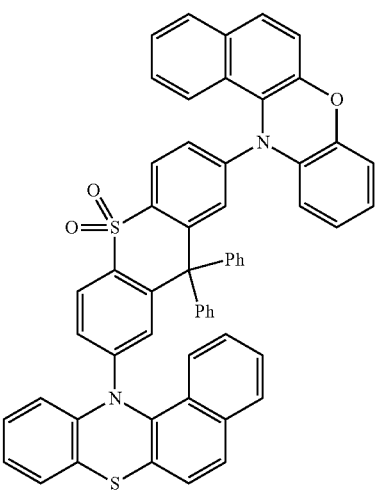

TD-34
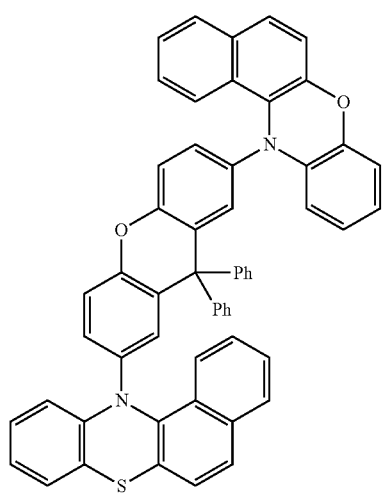
TD-35
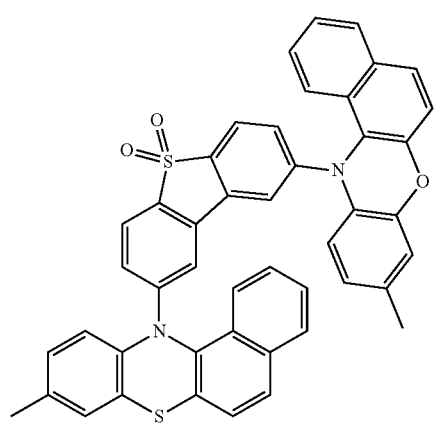
TD-36
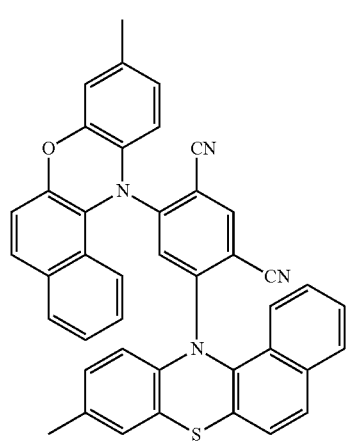
TD-37
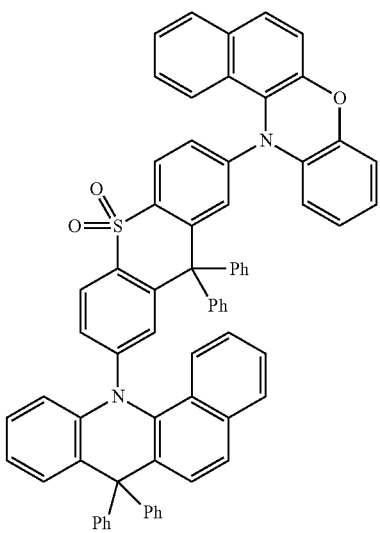
TD-38
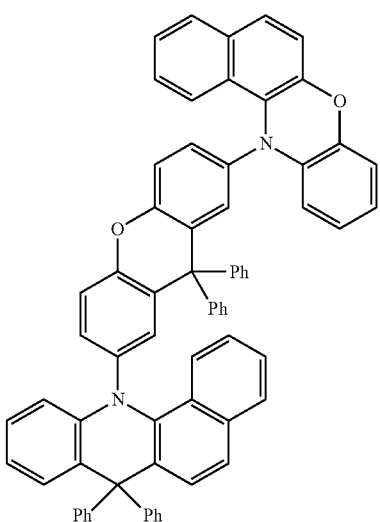
TD-39
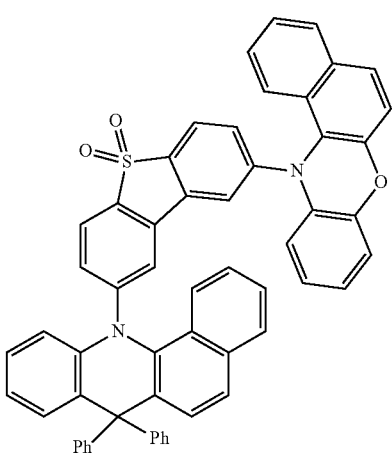

TD-40

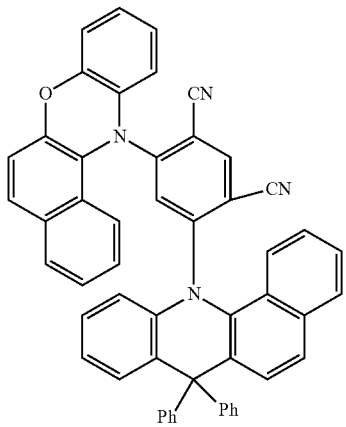

TD-41

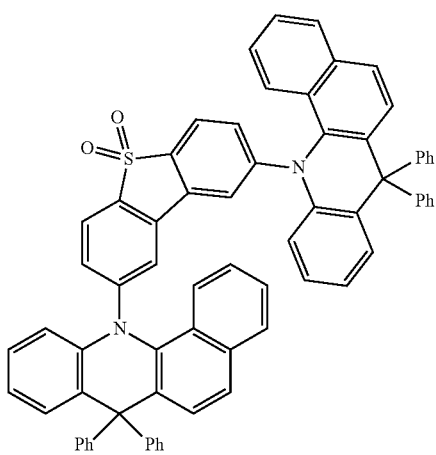

TD-42

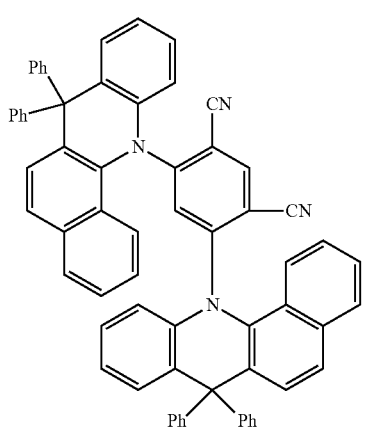

TD-43

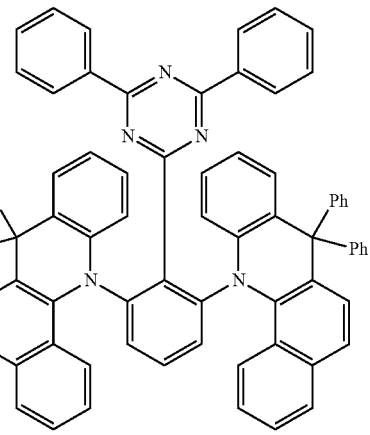

The heterocyclic compound according to an embodiment of the inventive concept may have an absolute value of the difference between the lowest excited singlet energy level S1 and the lowest excited triplet excitation energy level T1 of 0.2 eV or less. The heterocyclic compound according to an embodiment of the inventive concept has a small singlet-triplet energy gap, and therefore, may be utilized as an efficient thermally activated delayed fluorescence material.

Referring to FIGS. 1 and 2, the light emitting layer EML included in the organic electroluminescence device 10 according to an embodiment of the inventive concept will be described in more detail.

As described above, the light emitting layer EML includes the heterocyclic compound according to an embodiment of the inventive concept. For example, the light emitting layer EML includes the heterocyclic compound represented by Formula 1 described above.

The light emitting layer EML may include a host and a dopant. The dopant may include the heterocyclic compound according to an embodiment of the inventive concept. The dopant may be a thermally activated delayed fluorescence dopant, and the heterocyclic compound according to an embodiment of the inventive concept may be the dopant for thermally activated delayed fluorescence.

The host may employ a common material known in the art without limitation. For example, the host may include at least one of Bis[2-(diphenylphosphino)phenyl] ether oxide (DPEPO), 4,4'-Bis(carbazol-9-yl)biphenyl (CBP), 1,3-Bis(carbazol-9-yl)benzene (mCP), 2,8-Bis(diphenylphosphoryl)dibenzo[b,d]furan (PPF), 4,4',4"-Tris(carbazol-9-yl)-triphenylamine (TcTa), or 1,3,5-tris(N-phenylbenzimidazole-2-yl)benzene (TPBi). However, the embodiment of the inventive concept is not limited thereto, and may utilize, for example, tris(8-hydroxyquinolino)aluminum (Alq3), 4,4'-bis(N-carbazolyl)-1,1'-biphenyl (CBP), poly(n-vinylcabazole (PVK), 9,10-di(naphthalene-2-yl)anthracene (ADN), 4,4',4"-Tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4-bis(9-carbazolyl)-2,2'-dimethyl-biphenyl (CDBP), 2-Methyl-9,10-bis(naphthalen-2-yl)anthracene (MADN), bis[2-(diphenylphosphino)phenyl]ether oxide (DPEPO), Hexaphenyl cyclotriphosphazene (CP1), 1,4-Bis(triphenylsilyl)benzene (UGH2), Hexaphenylcyclotrisiloxane (DPSiO$_3$), Octaphenylcyclotetra siloxane (DPSiO$_4$), 2,8-Bis(diphenylphosphoryl)dibenzofuran (PPF), and/or the like, as a host material.

The light emitting layer EML may further include a dopant for thermally activated delayed fluorescence known in the art in addition to the heterocyclic compound according to an embodiment of the inventive concept. For example, as a dopant, the light emitting layer EML may further include at least one of 10-phenyl-10H, 10'H-spiro[acridine-9,9'-anthracene]-10'-one (ACRSA), 3,4,5,6-Tetra-9H-carbazol-9-yl-1,2-benzenedicarbonitrile (4CzPN), 2,4,5,6-Tetra-9H-carbazol-9-yl-isophthalonitrile (4CzIPN), Bis[4-9,9-dimethyl-9,10-dihydroacridine)phenyl]solfone (DMAC-DPS), and 2-phenoxazine-4,6-diphenyl-1,3,5-triazine (PSZ-TRZ). In addition, as a dopant material known in the art, the light emitting layer EML may further include a styryl derivative (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi)), perylene and a derivative thereof (for example, 2,5,5,8,11-tetra-t-butylperylene (TBP)), pyrene and a derivative thereof (for example, 2,5,5,8,11-tetra-t-butylperylene (TBP) and/or the like, such as 1,1-dipyrene, 1,4-dipyrenylbenzene, or 1,4-Bis (N, N-Diphenylamino)pyrene).

The light emitting layer EML may be a blue light emitting layer which emits blue light. The light emitting layer EML may be a light emitting layer which emits thermally activated delayed fluorescence. For example, the light emitting layer EML may be a blue light emitting layer which emits blue light through thermally activated delayed fluorescence.

The heterocyclic compound for an organic electroluminescence device according to an embodiment of the inventive concept may be utilized as a material for a light emitting layer, and may contribute to high efficiency and/or low driving voltage of the organic electroluminescence device.

The organic electroluminescence device according to an embodiment of the inventive concept is characterized by including the heterocyclic compound represented by Formula 1, may have improved efficiency, and may also have an effect of lowering the driving voltage.

Hereinafter, the inventive concept will be described in more detail with reference to the specific examples and comparative examples. The following examples are merely exemplary for the understanding of the inventive concept, and the scope of the inventive concept is not limited thereto.

SYNTHESIS EXAMPLE

A heterocyclic compound according to an embodiment of the inventive concept may be synthesized, for example, as follows. However, a method for synthesizing a heterocyclic compound according to an embodiment of the inventive concept is not limited thereto.

1. Synthesis Example 1: Synthesis of TD-1

To a flask containing 2,7-dichloro-9,9-dimethyl-9H-thioxanthene 10,10-dioxide (1 eq) and 12H-benzo[a]phenothiazine (2.2 eq), Pd(dba)$_3$ (0.03 eq), (t-Bu)$_3$P (0.06 eq), and toluene (based on 0.1 M 1 eq reagent) were added, and the mixture was subjected to reflux stirring for 5 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-1 (Yield 77.64%).

HRMS for $C_{47}H_{32}N_2O_2S_3$ $[M]^+$: calcd:752, found: 751

Elemental Analysis for calcd: C, 74.97; H, 4.28; N, 3.72; O, 4.25; S, 12.77.

2. Synthesis Example 2: Synthesis of TD-4

To a flask containing 4,6-dichloroisophthalonitrile (1 eq) and 12H-benzo[a]phenothiazine (2.2 eq), Pd(dba)$_3$ (0.03 eq), (t-Bu)$_3$P (0.06 eq), and toluene (based on 0.1 M 1 eq reagent) were added, and the mixture was subjected to reflux stirring for 5 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-4 (Yield 55.7%).

HRMS for $C_{40}H_{22}N_4S_2$ $[M]^+$: calcd: 622, found: 621.

Elemental Analysis for calcd: C, 77.15; H, 3.56; N, 9.00; S, 10.30.

3. Synthesis Example 3: Synthesis of TD-5

To a flask containing 2-(2,6-dibromophenyl)-4,6-diphenyl-1,3,5-triazine (1 eq) and 12H-benzo[a]phenothiazine (2.2 eq), Pd(dba)$_3$ (0.03 eq), (t-Bu)$_3$P (0.06 eq), and toluene (based on 0.1 M 1 eq reagent) were added, and the mixture was subjected to reflux stirring for 5 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-5 (Yield 71.4%).

HRMS for $C_{53}H_{33}N_5S_2$ $[M]^+$: calcd: 804, found: 803.

Elemental Analysis for calcd: C, 79.18; H, 4.14; N, 8.71; S, 7.98.

4. Synthesis Example 4: Synthesis of TD-6

To a flask containing 2,7-dibromo-9,9-dimethyl-9H-thioxanthene 10,10-dioxide (1 eq) and 12H-benzo[a]phenoxazine (2.2 eq), Pd(dba)$_3$ (0.03 eq), (t-Bu)$_3$P (0.06 eq), and toluene (based on 0.1 M 1 eq reagent) were added, and the mixture was subjected to reflux stirring for 5 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-6 (Yield 68.7%).

HRMS for $C_{47}H_{32}N_2O_4S$ $[M]^+$: calcd: 720, found: 719.

Elemental Analysis for calcd: C, 78.31; H, 4.47; N, 3.89; O, 8.88; S, 4.45

5. Synthesis Example 5: Synthesis of TD-9

To a flask containing 4,6-dichloroisophthalonitrile (1 eq) and 12H-benzo[a]phenoxazine (2.2 eq), Pd(dba)$_3$ (0.03 eq), (t-Bu)$_3$P (0.06 eq), and toluene (based on 0.1 M 1 eq reagent) were added, and the mixture was subjected to reflux stirring for 5 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-9 (Yield 65.1%).

HRMS for $C_{40}H_{22}N_4O_2$ [M]$^+$: calcd: 590, found: 589.
Elemental Analysis for calcd: C, 81.34; H, 3.75; N, 9.49; O, 5.42.

6. Synthesis Example 6: Synthesis of TD-10

To a flask containing 2-(2,6-dichlorophenyl)-4,6-diphenyl-1,3,5-triazine (1 eq) 12H-benzo[a]phenoxazine (2.2 eq), Pd(dba)$_3$ (0.03 eq), (t-Bu)$_3$P (0.06 eq), and toluene (based on 0.1 M 1 eq reagent) were added, and the mixture was subjected to reflux stirring for 5 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-10 (Yield 73.1%).

HRMS for $C_{53}H_{33}N_5O_2$ [M]$^+$: calcd: 771, found: 770.
Elemental Analysis for calcd: C, 82.47; H, 4.31; N, 9.07; O, 4.15.

7. Synthesis Example 7: Synthesis of TD-14

To a flask containing 4,6-dichloroisophthalonitrile (1 eq) and 7,7-dimethyl-7,12-dihydrobenzo[c]acridine (2.2 eq), Pd(dba)$_3$ (0.03 eq), (t-Bu)$_3$P (0.06 eq), and toluene (based on 0.1 M 1 eq reagent) were added, and the mixture was subjected to reflux stirring for 5 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-14 (Yield 77.4%).

HRMS for $C_{46}H_{34}N_4$ [M]$^+$: calcd: 642, found: 641.
Elemental Analysis for calcd: C, 85.95; H, 5.33; N, 8.72.

8. Synthesis Example 8: Synthesis of TD-15

To a flask containing 4,6-dichloroisophthalonitrile (1 eq) and 7,7-dimethyl-7,12-dihydrobenzo[c]acridine (2.2 eq), Pd(dba)$_3$ (0.03 eq), (t-Bu)$_3$P (0.06 eq), and toluene (based on 0.1 M 1 eq reagent) were added, and the mixture was subjected to reflux stirring for 5 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-15 (Yield 73.1%).

HRMS for $C_{59}H_{45}N_5$ [M]$^+$: calcd: 824, found: 823.
Elemental Analysis for calcd: C, 86.00; H, 5.50; N, 8.50.

9. Synthesis Example 9: Synthesis of TD-23

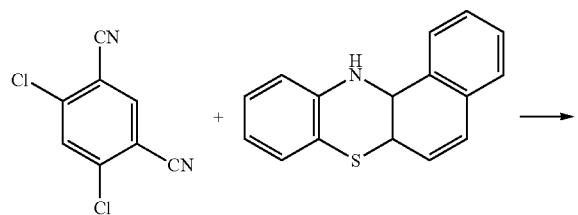

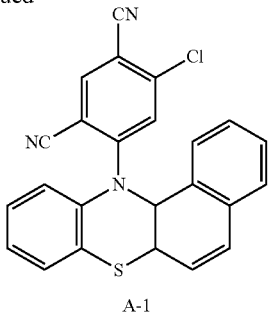

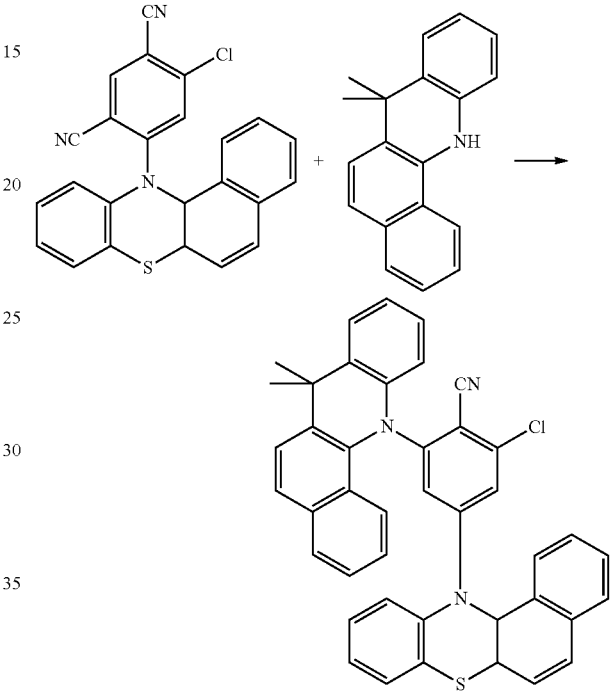

Synthesis of A-1

To a flask containing 4,6-dichloroisophthalonitrile (1 eq) and 12H-benzo[a]phenothiazine (0.9 eq), Pd(dba)$_3$ (0.03 eq), (t-Bu)$_3$P (0.06 eq), and toluene (based on 0.1 M 1 eq reagent) were added, and the mixture was subjected to reflux stirring for 3 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain A-1 (Yield 56.4%).

HRMS for $C_{24}H_{12}ClN_3S$ [M]$^+$: calcd: 409, found: 408.
Elemental Analysis for calcd: C, 70.33; H, 2.95; Cl, 8.65; N, 10.25; S, 7.82.

Synthesis of TD-23

To a flask containing A-1 (1 eq) and 7,7-dimethyl-7,12-dihydrobenzo[c]acridine (1.2 eq), Pd(dba)$_3$ (0.03 eq), (t-Bu)$_3$P (0.06 eq), and toluene (based on 0.1 M 1 eq reagent) were added, and the mixture was subjected to reflux stirring for 6 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-23 (Yield 77.8%).

HRMS for $C_{43}H_{28}N_4S$ [M]$^+$: calcd: 632, found: 631.

Elemental Analysis for calcd: C, 81.62; H, 4.46; N, 8.85; S, 5.07.

10. Synthesis Example 10: Synthesis of TD-24

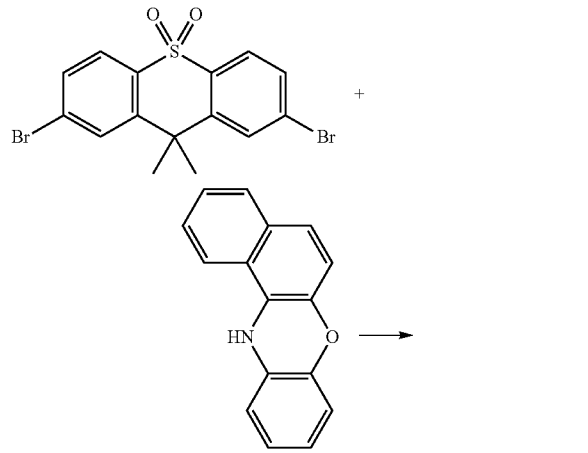

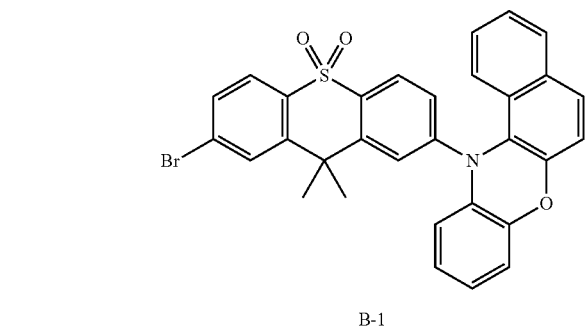

B-1

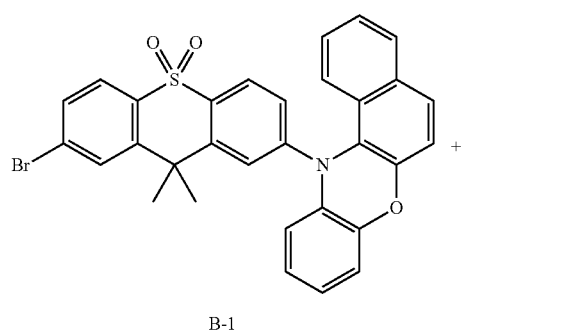

B-1

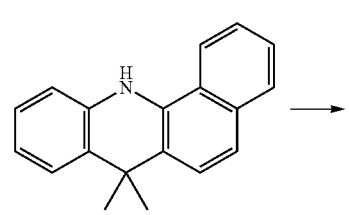

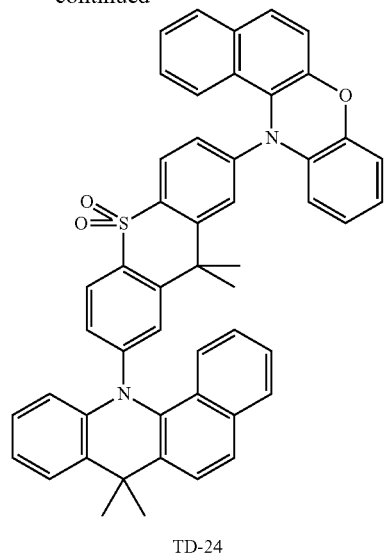

TD-24

Synthesis of B-1

To a flask containing 2,7-dibromo-9,9-dimethyl-9H-thioxanthene 10,10-dioxide (1 eq) and 12H-benzo[a]phenoxazine (0.9 eq), Pd(dba)$_3$ (0.03 eq), (t-Bu)$_3$P (0.06 eq), and toluene (based on 0.1 M 1 eq reagent) were added, and the mixture was subjected to reflux stirring for 4 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain B-1 (Yield 51.4%).

HRMS for $C_{31}H_{22}BrNO_3S$ [M]$^+$: calcd: 568, found: 567.

Elemental Analysis for calcd: C, 65.50; H, 3.90; Br, 14.06; N, 2.46; O, 8.44; S, 5.64.

Synthesis of TD-24

To a flask containing B-1 (1 eq) and 7,7-dimethyl-7,12-dihydrobenzo[c]acridine (1.2 eq), Pd(dba)$_3$ (0.03 eq), (t-Bu)$_3$P (0.06 eq), and toluene (based on 0.1 M 1 eq reagent) were added, and the mixture was subjected to reflux stirring for 6 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-24 (Yield 81.8%).

HRMS for $C_{50}H_{38}N_2O_3S$ [M]$^+$: calcd: 746, found: 745.

Elemental Analysis for calcd: C, 80.40; H, 5.13; N, 3.75; O, 6.43; S, 4.29.

11. Synthesis Example 11: Synthesis of TD-28

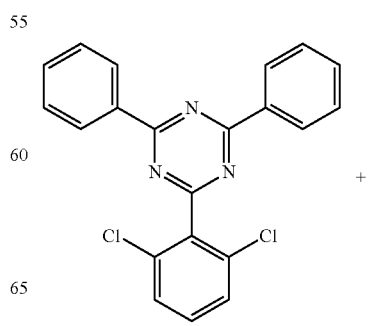

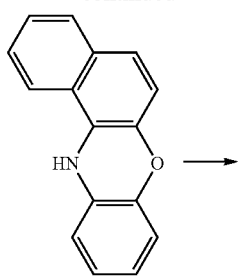

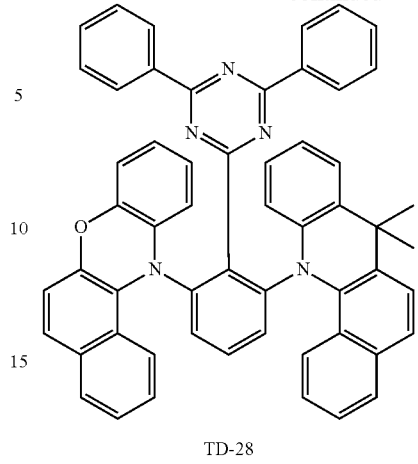

TD-28

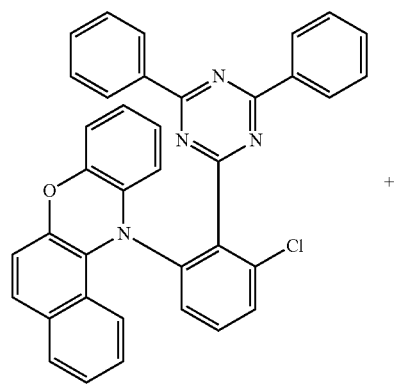

C-1

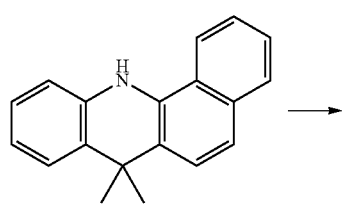

Synthesis of C-1

To a flask containing 2-(2,6-dichlorophenyl)-4,6-diphenyl-1,3,5-triazine (1 eq) and 12H-benzo[a]phenoxazine (0.9 eq), Pd(dba)$_3$ (0.03 eq), (t-Bu)$_3$P (0.06 eq), and toluene (based on 0.1 M 1 eq reagent) were added, and the mixture was subjected to reflux stirring for 4 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain C-1 (Yield 55.4%).

HRMS for $C_{37}H_{23}ClN_4O$ [M]+: calcd: 575, found: 574.

Elemental Analysis for calcd: C, 77.28; H, 4.03; Cl, 6.16; N, 9.74; O, 2.78.

Synthesis of TD-28

To a flask containing C-1 (1 eq) and 7,7-dimethyl-7,12-dihydrobenzo[c]acridine (1.2 eq), Pd(dba)$_3$ (0.03 eq), (t-Bu)$_3$P (0.06 eq), and toluene (based on 0.1 M 1 eq reagent) were added, and the mixture was subjected to reflux stirring for 6 hours. Then, the stirred mixture was cooled to room temperature, extracted with MC, and washed with distilled water. Thereafter, the washed mixture was dried with MgSO$_4$, distilled under reduced pressure, and the residue was separated into a column to obtain TD-28 (Yield 81.8%).

HRMS for $C_{56}H_{39}N_5O$ [M]+: calcd: 797, found: 796.

Elemental Analysis for calcd: C, 84.29; H, 4.93; N, 8.78; O, 2.00.

The synthesis examples described above are only exemplary, and the reaction conditions may be changed as needed. In addition, a compound according to an embodiment of the inventive concept may be synthesized to have various substituents utilizing suitable methods and materials known in the art. By introducing various substituents into a core structure, the compound may have properties suitable to be utilized in an organic electroluminescence device.

Device Production Example

Utilizing the above-described compounds TD-1, TD-4, TD-5, TD-6, TD-9, TD-10, TD-14, TD-15, TD-23, TD-24, and TD-28 as a light emitting layer dopant material, organic electroluminescence devices of Examples 1 to 11 were manufactured respectively.

Example Compound
TD-1
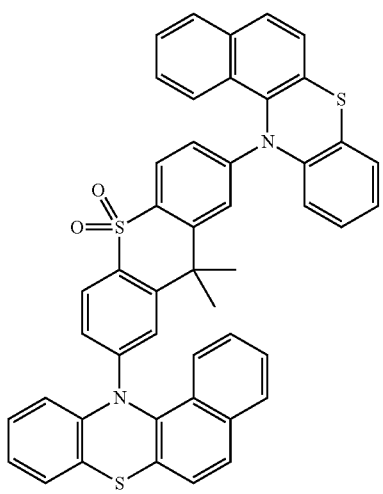
TD-6
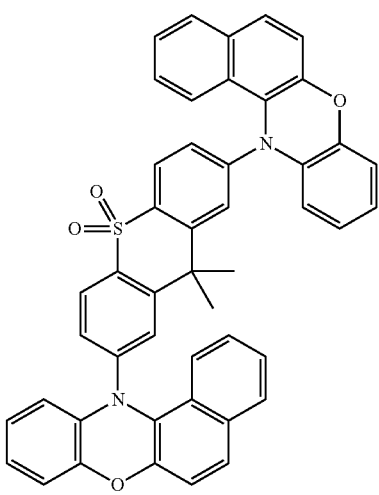
TD-4
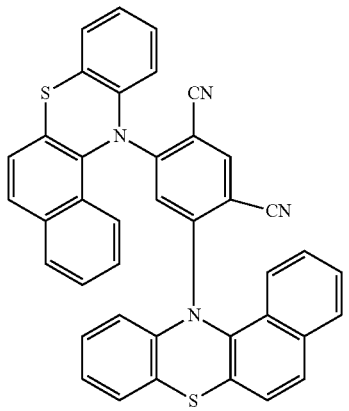
TD-9
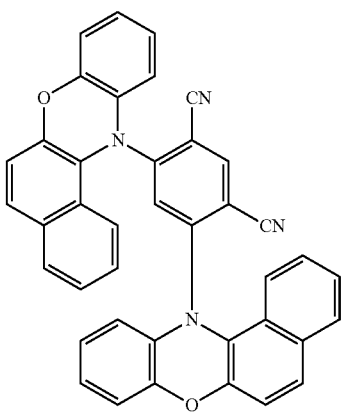
TD-5
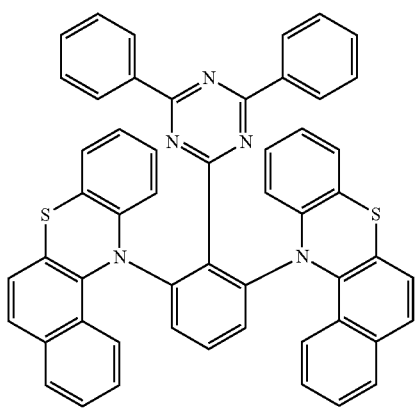
TD-10
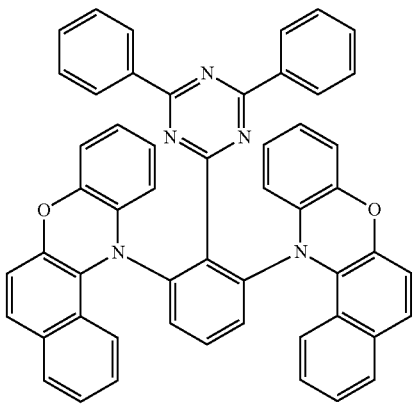

TD-14
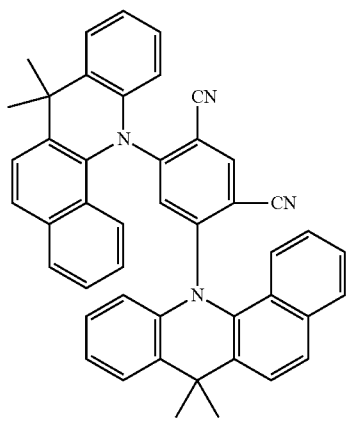
TD-24
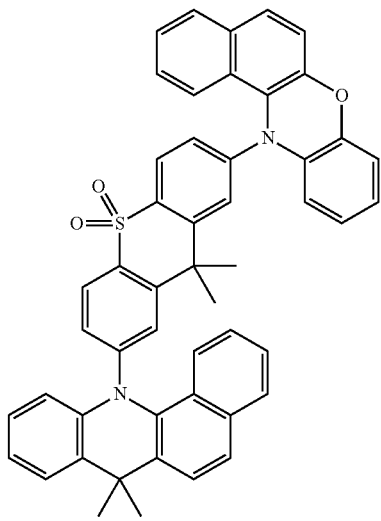
TD-15
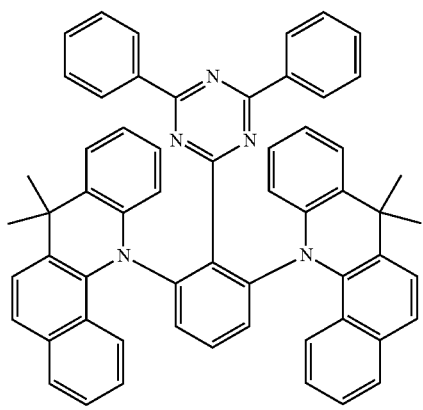
TD-28
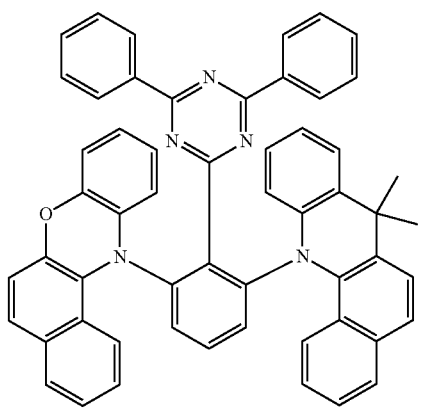
TD-23
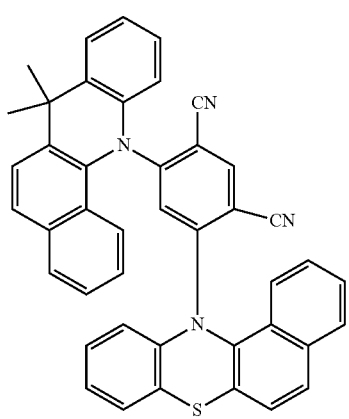
Utilizing the following comparative compounds TF-1 and TF-2 as a light emitting layer dopant material, organic electroluminescence devices of Comparative Examples 1 and 2 were manufactured.
Comparative Example Compound
TF-1
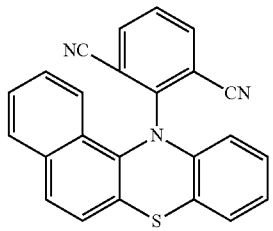

-continued

TF-2

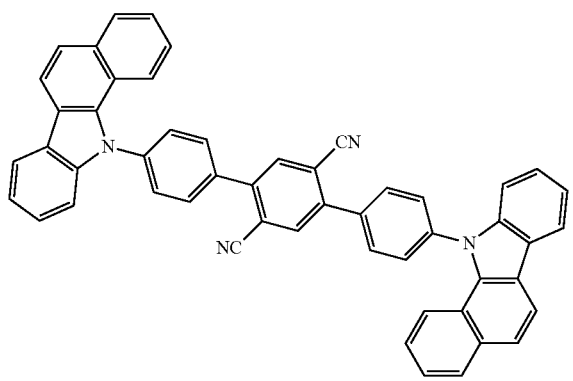

The organic electroluminescence devices of Examples 1 to 11 and Comparative Examples 1 and 2 were manufactured as follows.

An ITO glass substrate was cut to a size of 50 mm×50 mm×0.5 mm, ultrasonically washed with isopropyl alcohol and pure water for 10 minutes each, irradiated with ultraviolet rays for 10 minutes, exposed to ozone, and cleaned. Then, the ITO glass substrate was installed in a vacuum deposition apparatus. NPB was vacuum deposited on an upper portion (e.g., an upper surface, such as the surface coated with ITO) of the ITO glass substrate to form a hole injection layer having a thickness of 40 Å, and mCP was vacuum deposited on an upper portion (e.g., an upper surface) of the hole injection layer to form a hole transport layer having a thickness of 10 Å. An example compound or a comparative example compound, and a DPEPO, which is a host, were co-deposited on an upper portion (e.g., an upper surface) of the hole transport layer at a weight ratio of 15:85 to form a light emitting layer having a thickness of 200 Å. The ETL1 material below was deposited on a upper portion (e.g., an upper surface) of the light emitting layer to form an electron transport layer having a thickness of 300 Å, LiF was deposited to form an electron injection layer having a thickness of 10 Å, and Al was deposited to form a second electrode having a thickness of 1200 Å.

ETL1

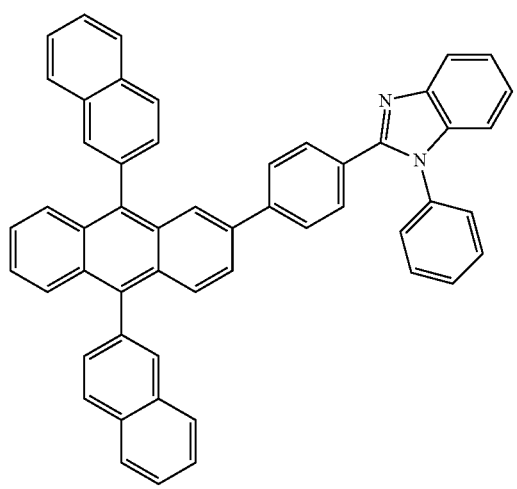

The driving voltage, the light emitting efficiency, and the external quantum efficiency (EQE) of the organic electroluminescence devices according to Examples 1 to 11 and Comparative Examples 1 and 2 were measured and are shown in Table 1 below.

TABLE 1

| | Light emitting layer dopant material | Driving voltage (V) | Light emitting efficiency (cd/A) | EQE (%) |
|---|---|---|---|---|
| Example 1 | TD-1 | 5.25 | 10.22 | 6.9 |
| Example 2 | TD-4 | 5.44 | 10.1 | 6.78 |
| Example 3 | TD-5 | 5.62 | 10.7 | 6.98 |
| Example 4 | TD-6 | 5.7 | 11.76 | 6.88 |
| Example 5 | TD-9 | 5.68 | 12.54 | 7.0 |
| Example 6 | TD-10 | 5.1 | 10.88 | 7.0 |
| Example 7 | TD-14 | 5.2 | 11.1 | 7.1 |
| Example 8 | TD-15 | 4.9 | 13.6 | 7.8 |
| Example 9 | TD-23 | 5.34 | 12.5 | 7.2 |
| Example 10 | TD-24 | 5.0 | 11.7 | 6.9 |
| Example 11 | TD-28 | 4.8 | 12.7 | 7.5 |
| Comparative Example 1 | TF-1 | 5.56 | 8.7 | 5.9 |
| Comparative Example 2 | TF-2 | 5.78 | 9.1 | 6.4 |

Referring to the results shown in Table 1, it can be seen that Examples 1 to 11 are excellent in efficiency as compared with Comparative Examples 1 and 2 in which a thermally activated delayed fluorescence material known in the art was utilized. Comparative Example 1 has a structure in which only one electron donating group is included, and thus has lower efficiency than Examples 1 to 11 in which two electron donating groups are included. Although Comparative Example 2 includes two electron donating groups, each electron donating group includes a 5-membered ring, and thus efficiency was lower than that of Examples 1 to 11, in which each electron donating group thereof includes a hexagonal ring. An organic electroluminescence device utilizing a heterocyclic compound according to an embodiment of the inventive concept as a light emitting layer material is excellent in efficiency, and has an effect of lowering the driving voltage.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:

1. An organic electroluminescence device comprising:
    a first electrode;
    a hole transport region on the first electrode;
    a light emitting layer on the hole transport region;
    an electron transport region on the light emitting layer; and
    a second electrode on the electron transport region, wherein
    the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide thereof, and the light emitting layer comprises a heterocyclic compound represented by Formula 1 below:

$$D_1-A-D_2 \qquad \text{Formula 1}$$

wherein in Formula 1, $D_1$ and $D_2$ are each independently represented by Formula 2 below, and A is represented by any one of Formulas 3-1 to 3-3 below, Formula 2

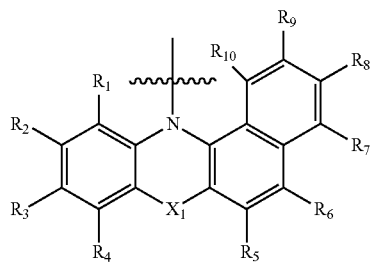

Formula 3-1

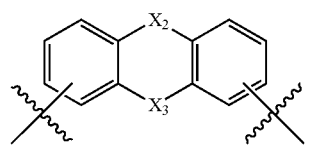

Formula 3-2

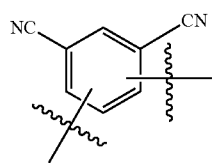

Formula 3-3

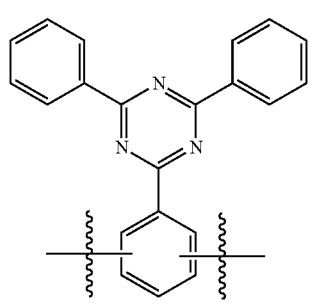

wherein in Formula 2, $X_1$ is S, O, or $CY_1Y_2$, and $R_1$ to $R_{10}$, $Y_1$ and $Y_2$ are each independently a hydrogen atom, a deuterium atom, a substituted or unsubstituted alkyl group having 1 to 10 carbon atoms, or a substituted or unsubstituted aryl group having 6 to 30 ring-forming carbon atoms, and wherein in Formula 3-1, $X_2$ is $SO_2$ or O, $X_3$ is a direct linkage or $CY_3Y_4$, and $Y_3$ and $Y_4$ are each independently a hydrogen atom, a deuterium atom, a substituted or unsubstituted alkyl group having 1 to 10 carbon atoms, or a substituted or unsubstituted aryl group having 6 to 30 ring-forming carbon atoms.

2. The organic electroluminescence device of claim 1, wherein

A is represented by any one of Formulas 4-1 to 4-3 below:

Formula 4-1

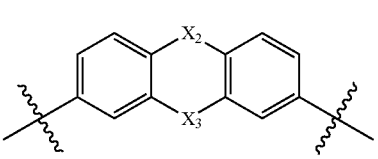

Formula 4-2

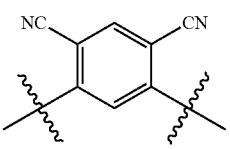

Formula 4-3

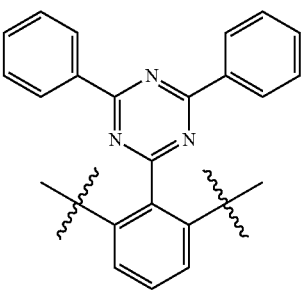

wherein in Formula 4-1, $X_2$ and $X_3$ are same as defined in claim 1.

3. The organic electroluminescence device of claim 1, wherein

A represented by Formula 3-1 is represented by any one of Formulas 3-1-1 to 3-1-3 below:

Formula 3-1-1

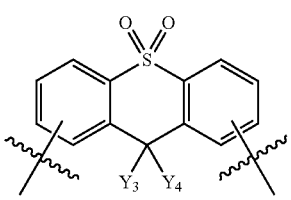

Formula 3-1-2

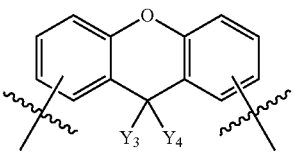

Forula 3-1-3

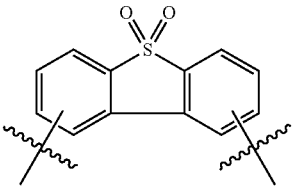

wherein in Formulas 3-1-1 and 3-1-2, $Y_3$ and $Y_4$ are same as defined in claim 1.

4. The organic electroluminescence device of claim 1, wherein

A represented by Formula 3-1 above may be represented by any one of Formulas 3-1-4 to 3-1-6 below:

Formula 3-1-4

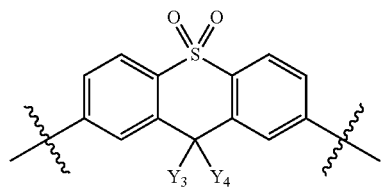

Formula 3-1-5

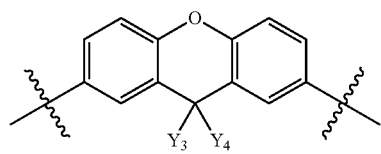

Forula 3-1-6

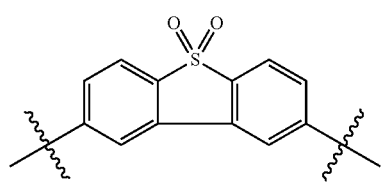

wherein in Formulas 3-1-4 and 3-1-5, $Y_3$ and $Y_4$ are same as defined in claim 1.

5. The organic electroluminescence device of claim 1, wherein in at least one of $D_1$ and $D_2$, $X_1$ is $CY_1Y_2$, $Y_1$ and $Y_2$ are same as defined in claim 1, and A is represented by Formula 3-3.

6. The organic electroluminescence device of claim 5, wherein $Y_1$ and $Y_2$ are each independently a substituted or unsubstituted alkyl group having 1 to 5 carbon atoms.

7. The organic electroluminescence device of claim 1, wherein $D_1$ and $D_2$ are the same.

8. The organic electroluminescence device of claim 1, wherein $D_1$ and $D_2$ are different from each other.

9. The organic electroluminescence device of claim 1, wherein the light emitting layer comprises a host and a dopant, and the dopant comprises the heterocyclic compound represented by Formula 1.

10. The organic electroluminescence device of claim 9, wherein the dopant is a thermally activated delayed fluorescence dopant.

11. The organic electroluminescence device of claim 1, wherein the heterocyclic compound represented by Formula 1 is at least one selected from the compounds represented by Compound Group 1 below:

Compound group 1

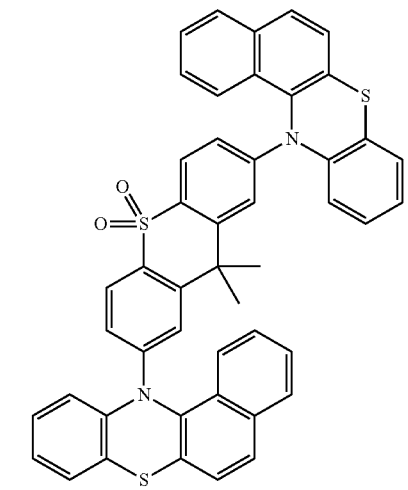
TD-1

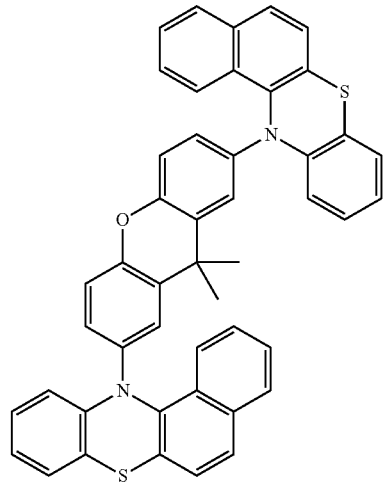
TD-2

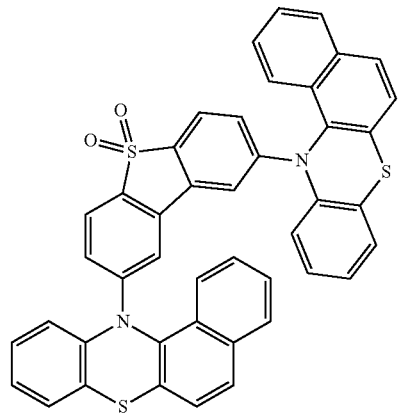
TD-3

-continued
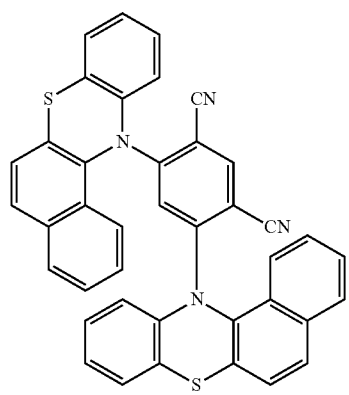
TD-4
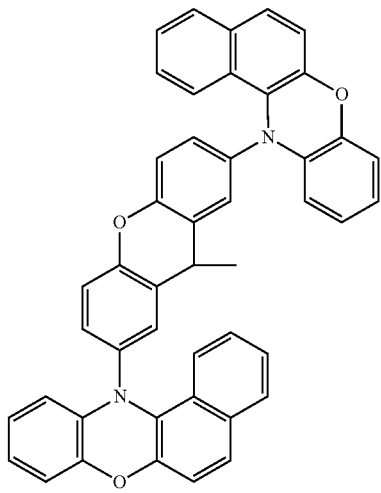
TD-7
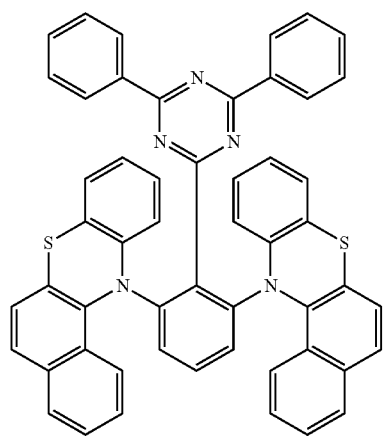
TD-5
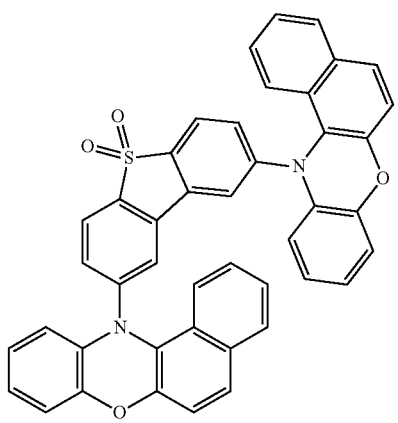
TD-8
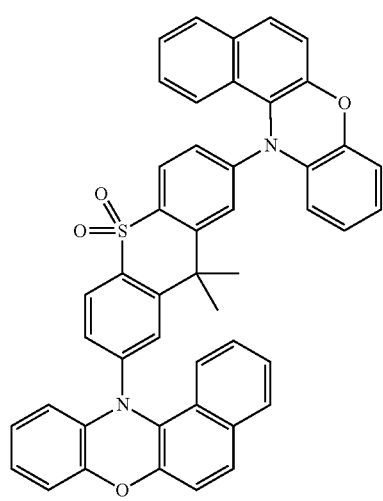
TD-6
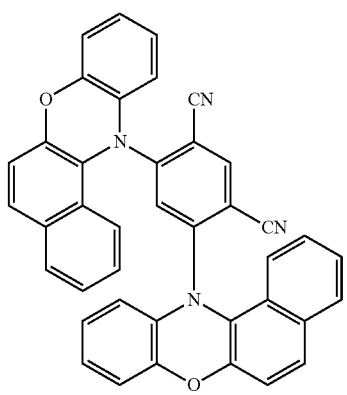
TD-9

TD-10
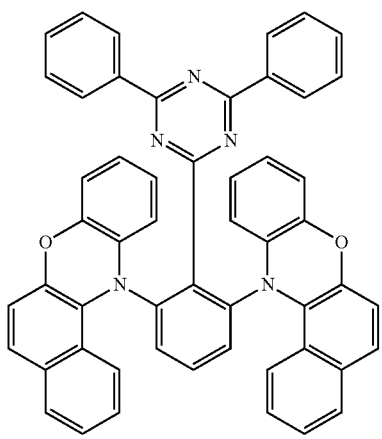
TD-11
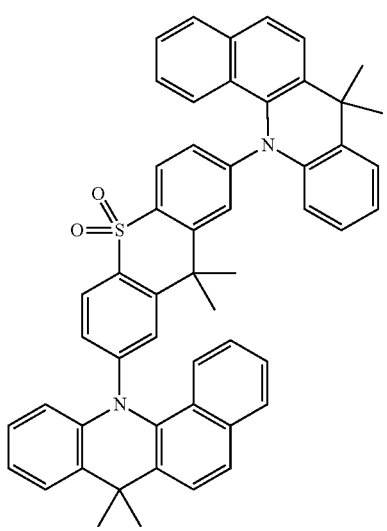
TD-12
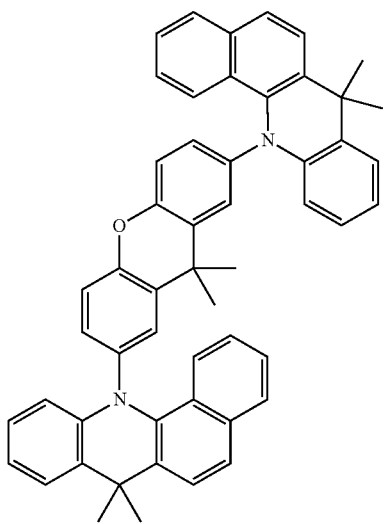
TD-13
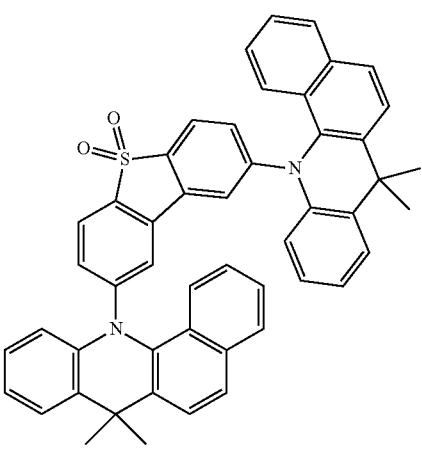
TD-14
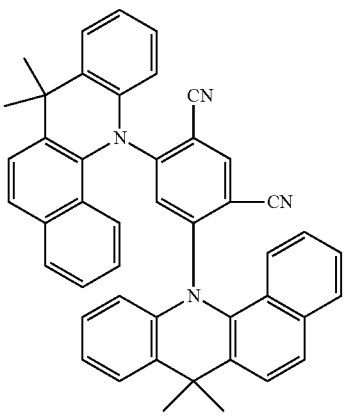
TD-15
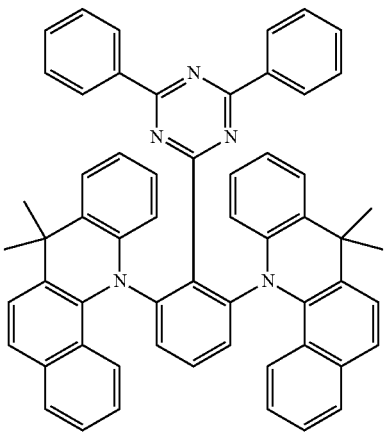

TD-16
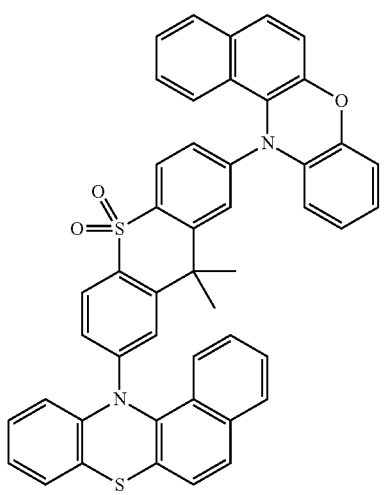
TD-17
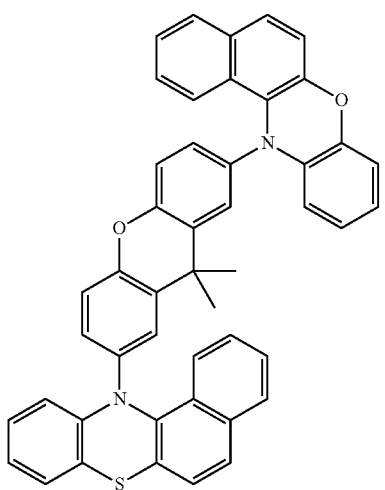
TD-18
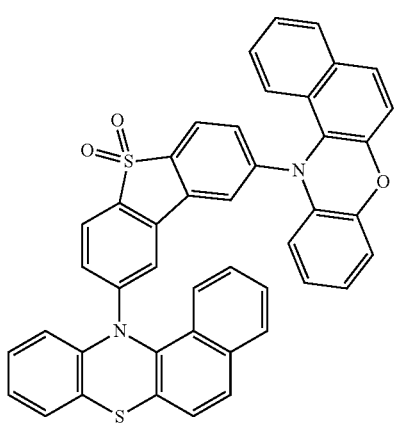
TD-19
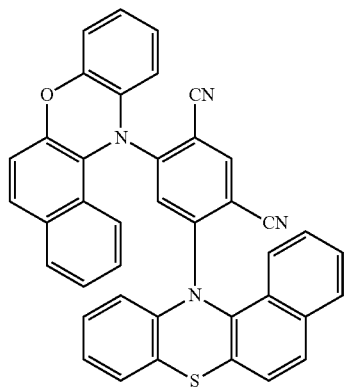
TD-20
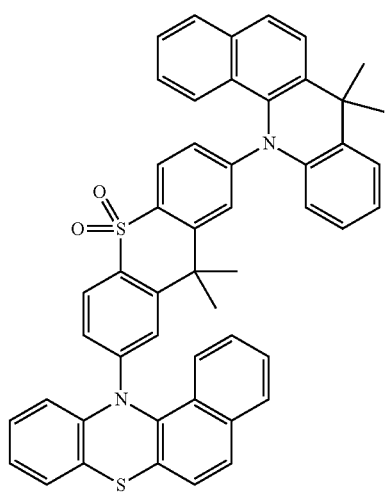
TD-21
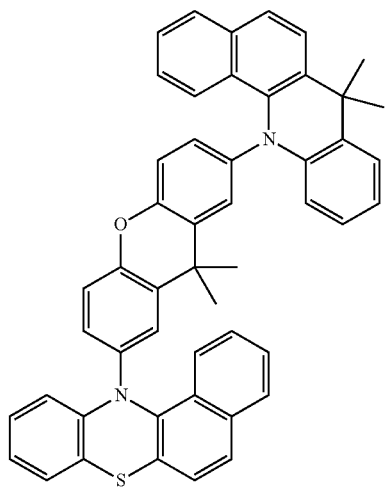

TD-22
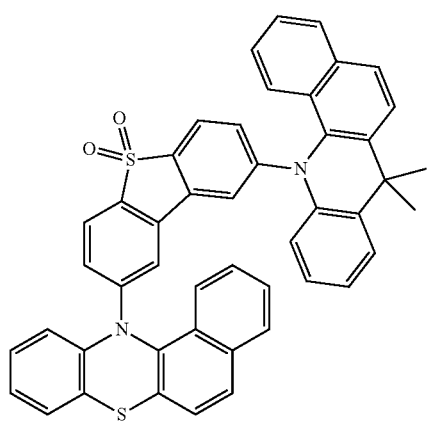
TD-23
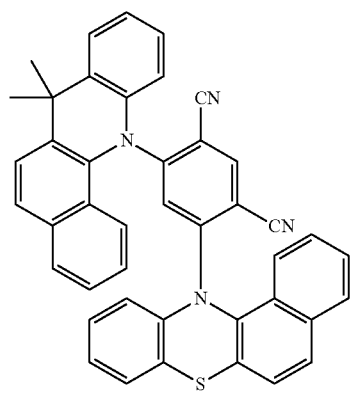
TD-24
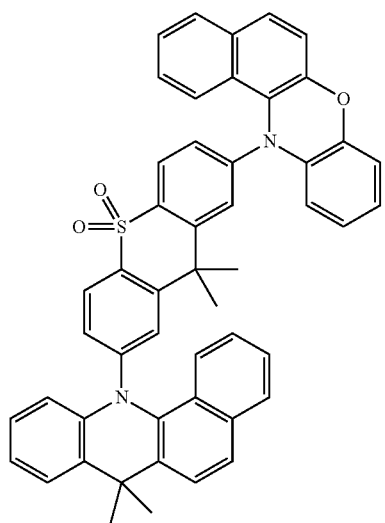
TD-25
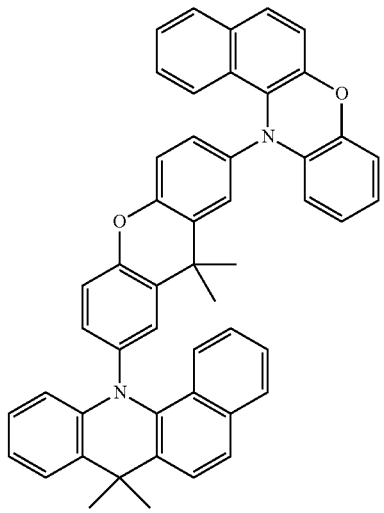
TD-26
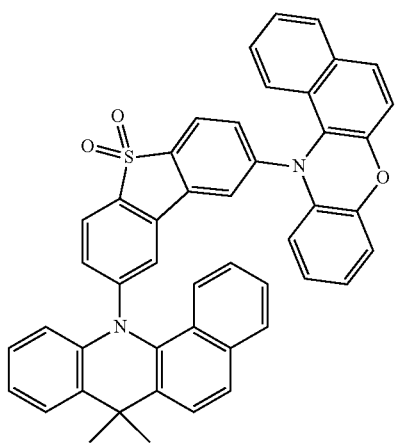
TD-27
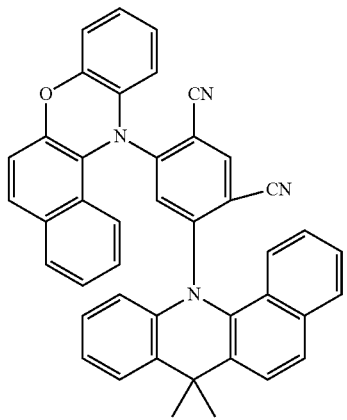

TD-28
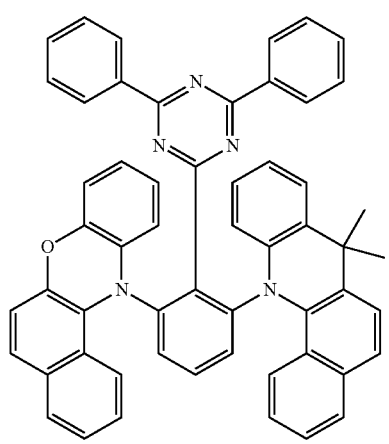
TD-29
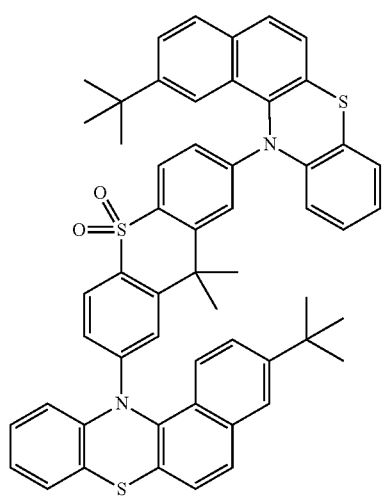
TD-30
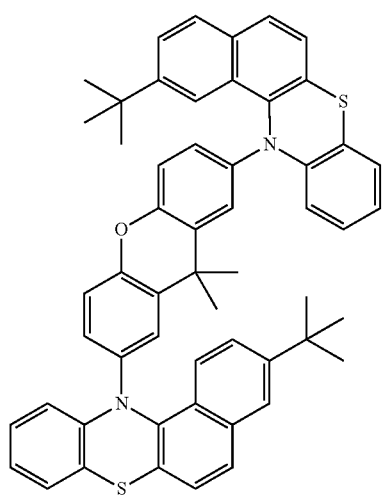
TD-31
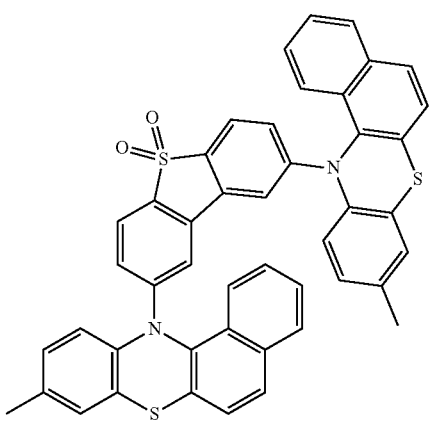
TD-32
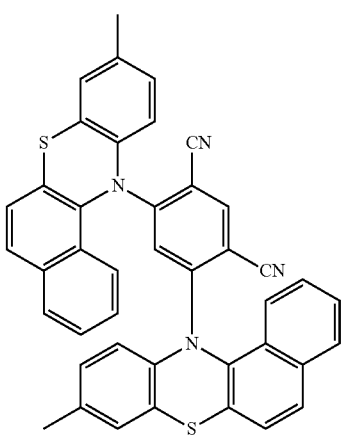
TD-33
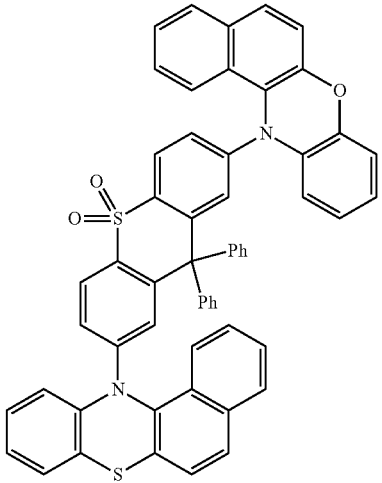

TD-34
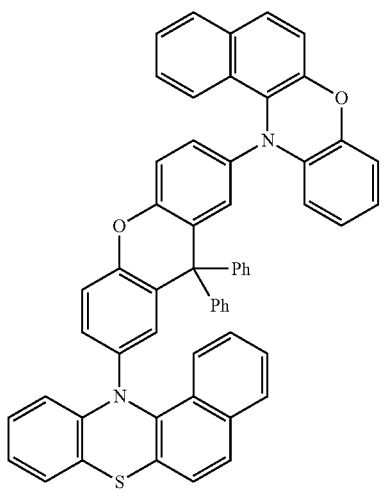
TD-37
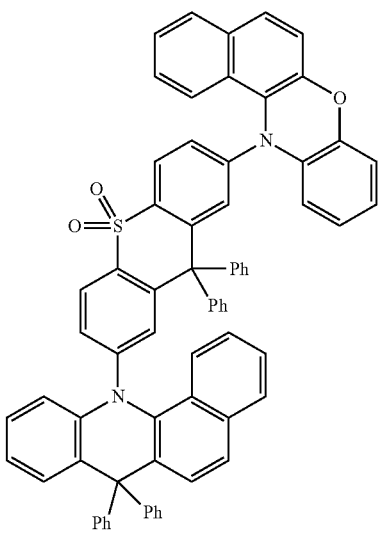
TD-35
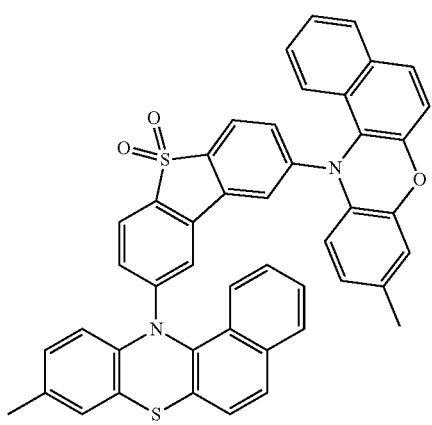
TD-38
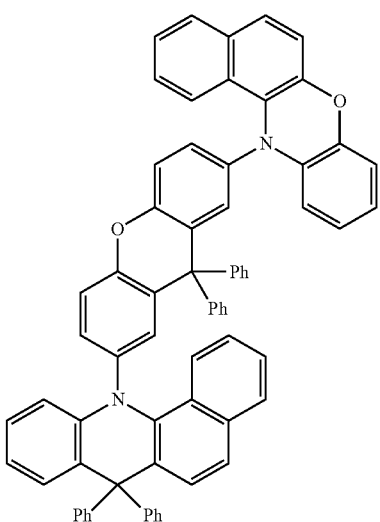
TD-36
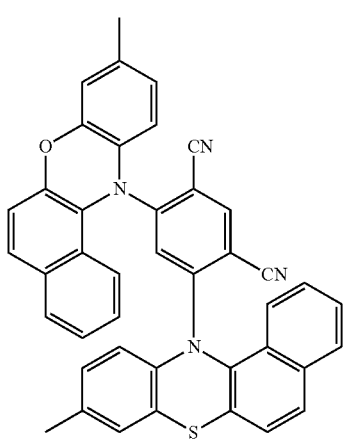
TD-39
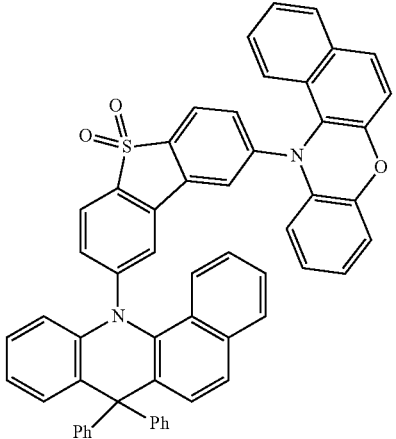

TD-40
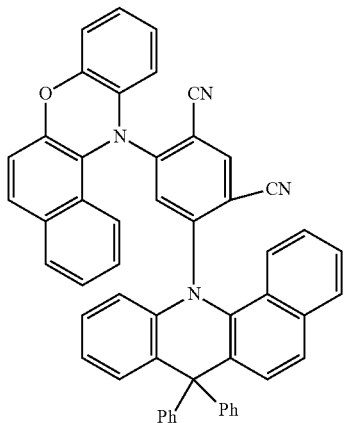
TD-41
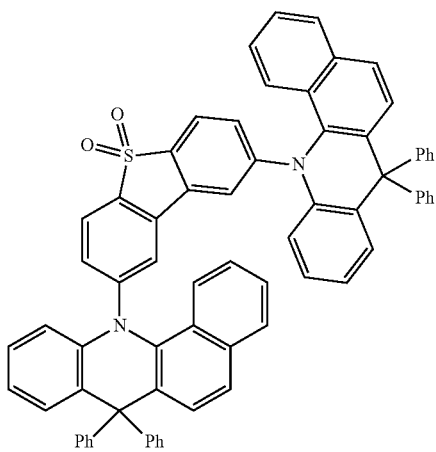
TD-42
TD-43
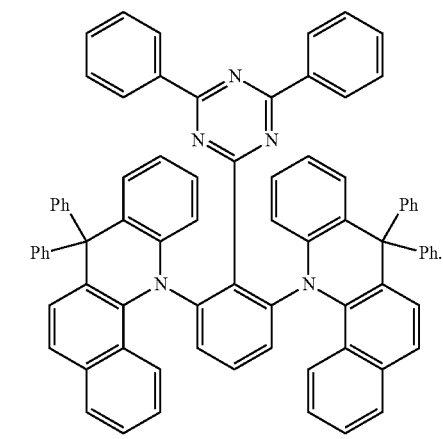
12. A heterocyclic compound represented by Formula 1 below:
$$D_1\text{-}A\text{-}D_2 \qquad \text{Formula 1}$$
wherein in Formula 1,
$D_1$ and $D_2$ are each independently represented by Formula 2 below, and
A is represented by any one of Formulas 3-1 to 3-3 below,
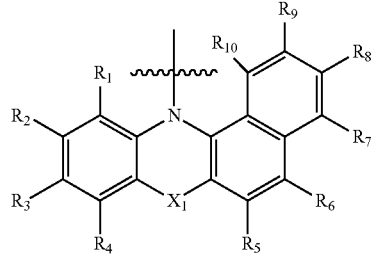
Formula 2
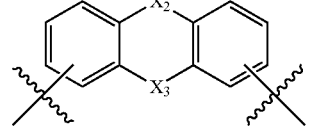
Formula 3-1
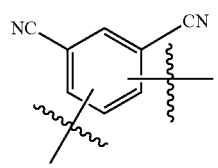
Formula 3-2
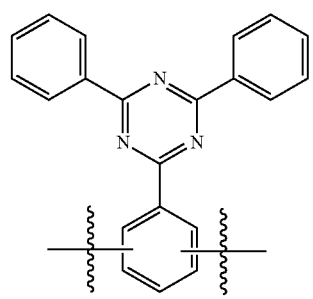
Formula 3-3 wherein in Formula 2, $X_1$ is S, O, or $CY_1Y_2$, and $R_1$ to $R_{10}$, $Y_1$ and $Y_2$ are each independently a hydrogen atom, a deuterium atom, a substituted or unsubstituted alkyl group having 1 to 10 carbon atoms, or a substituted or unsubstituted aryl group having 6 to 30 ring-forming carbon atoms, and wherein in Formula 3-1, $X_2$ is $SO_2$ or O, $X_3$ is a direct linkage or $CY_3Y_4$, and $Y_3$ and $Y_4$ are each independently a hydrogen atom, a deuterium atom, a substituted or unsubstituted alkyl group having 1 to 10 carbon atoms, or a substituted or unsubstituted aryl group having 6 to 30 ring-forming carbon atoms.

13. The heterocyclic compound of claim 12, wherein A is represented by any one of Formulas 4-1 to 4-3 below:

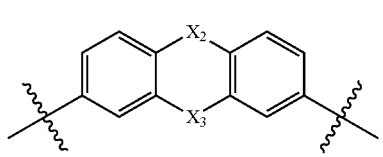

Formula 4-1

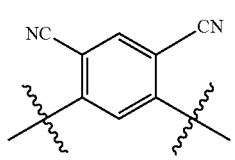

Formula 4-2

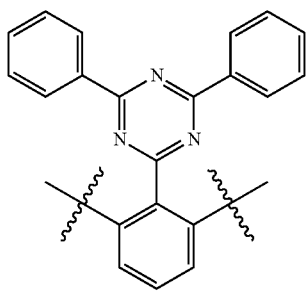

Formula 4-3 wherein in Formula 4-1, $X_2$ and $X_3$ are same as defined in claim 12.

14. The heterocyclic compound of claim 12, wherein A represented by Formula 3-1 is represented by any one of Formulas 3-1-1 to 3-1-3 below:

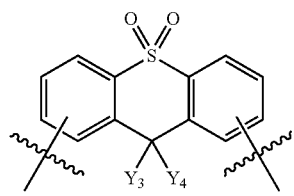

Formula 3-1-1

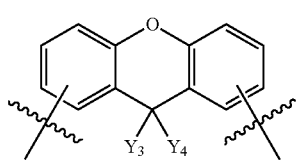

Formula 3-1-2

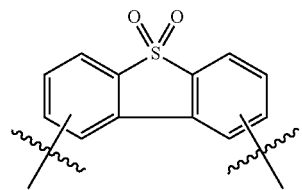

Forula 3-1-3 wherein in Formulas 3-1-1 and 3-1-2, $Y_3$ and $Y_4$ are same as defined in claim 12.

15. The heterocyclic compound of claim 12, wherein A represented by Formula 3-1 is represented by any one of Formulas 3-1-4 to 3-1-6 below:

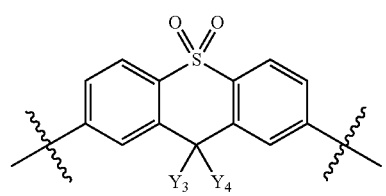

Formula 3-1-4

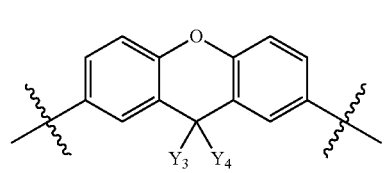

Formula 3-1-5

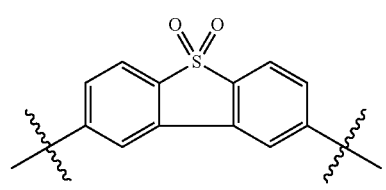

Forula 3-1-6 wherein in Formulas 3-1-4 and 3-1-5, $Y_3$ and $Y_4$ are same as defined in claim 12.

16. The heterocyclic compound of claim 12, wherein in at least one of $D_1$ and $D_2$, $X_1$ is $CY_1Y_2$, $Y_1$ and $Y_2$ are same as defined in claim 12, and A is represented by Formula 3-3.

17. The heterocyclic compound of claim 16, wherein $Y_1$ and $Y_2$ are each independently a substituted or unsubstituted alkyl group having 1 to 5 carbon atoms.

18. The heterocyclic compound of claim 12, wherein $D_1$ and $D_2$ are the same.

19. The heterocyclic compound of claim 12, wherein $D_1$ and $D_2$ are different from each other.

20. The heterocyclic compound of claim 12, wherein the heterocyclic compound represented by Formula 1 is at least one selected from the compounds represented by Compound Group 1 below:
Compound group 1
TD-1
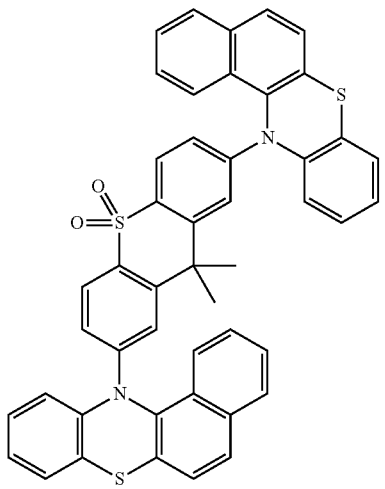
TD-2
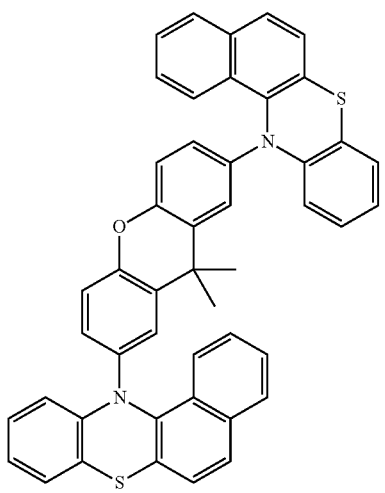
TD-3
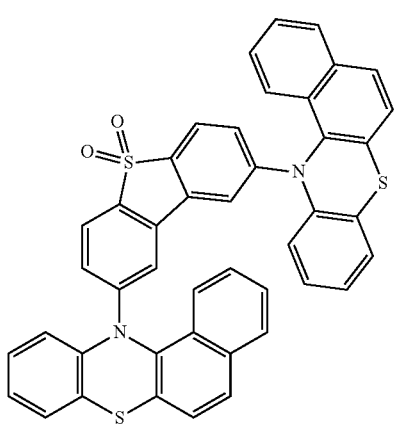
TD-4
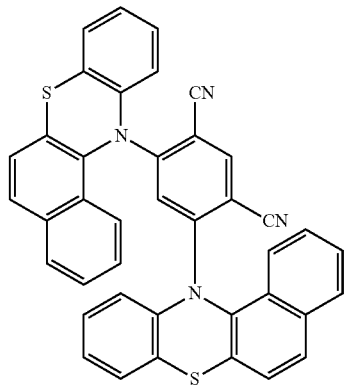
TD-5
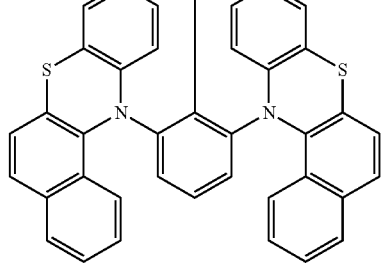
TD-6
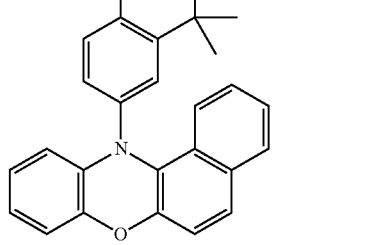

TD-7
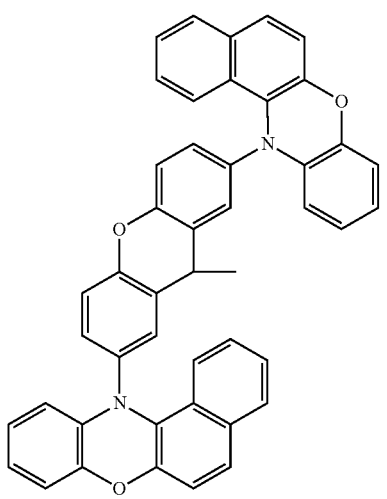
TD-8
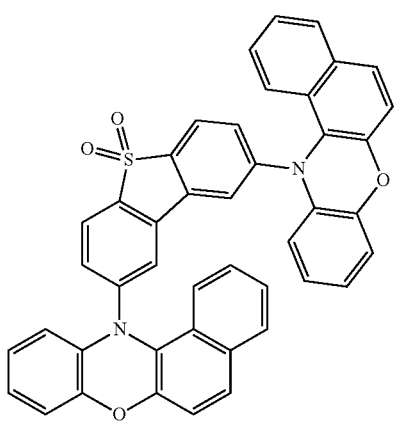
TD-9
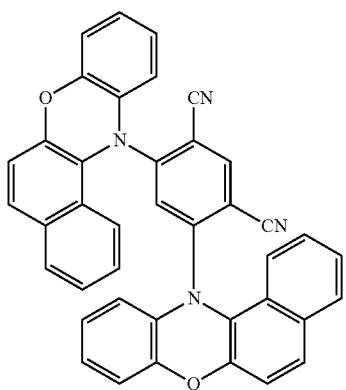
TD-10
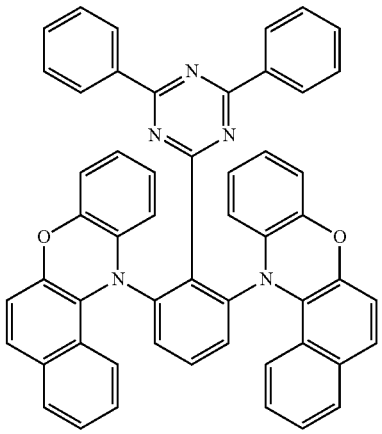
TD-11
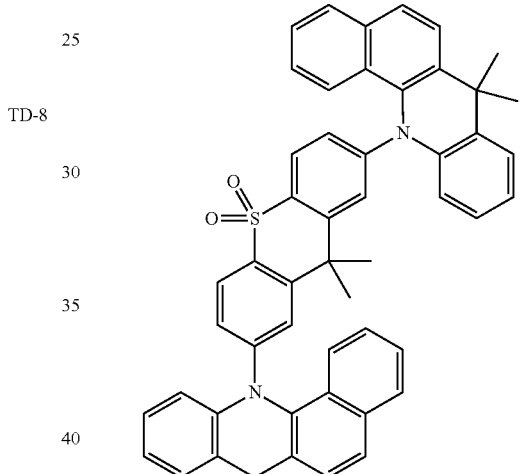
TD-12
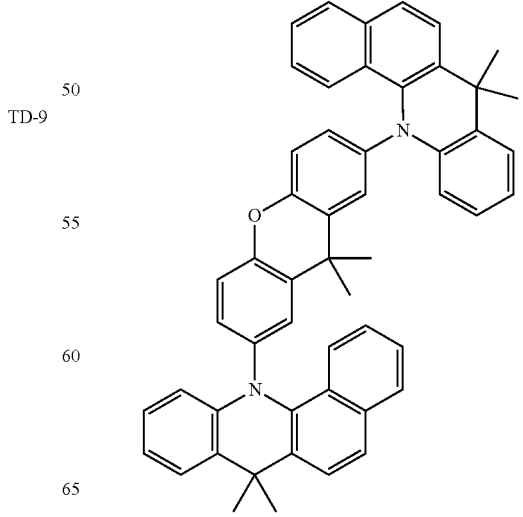

TD-13
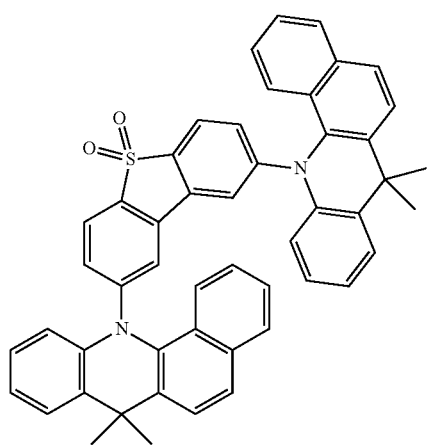
TD-16
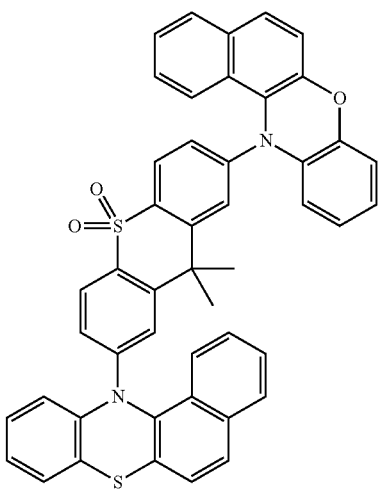
TD-14
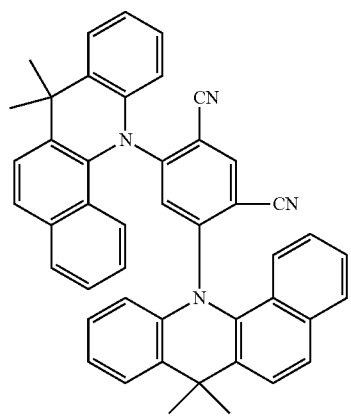
TD-17
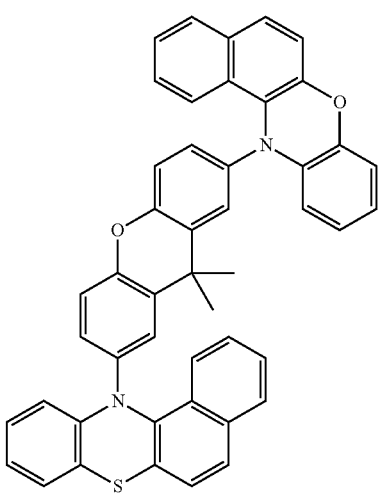
TD-15
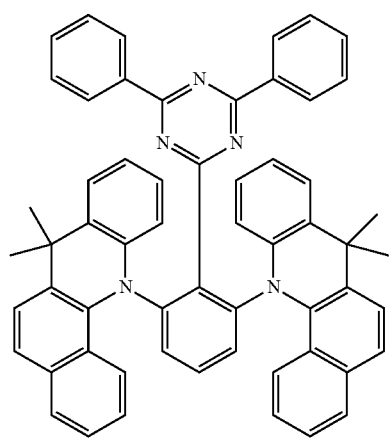
TD-18
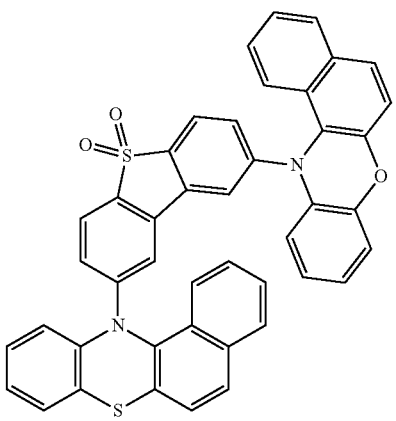

TD-19
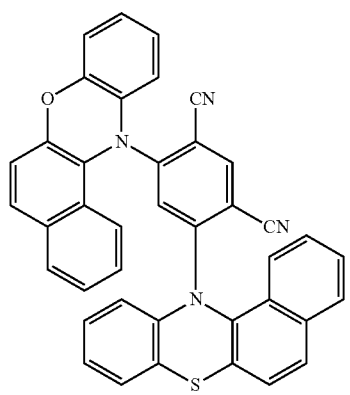
TD-20
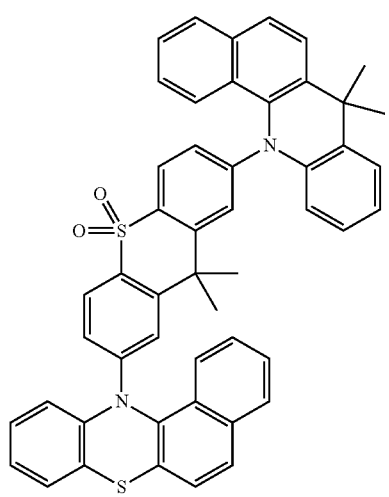
TD-21
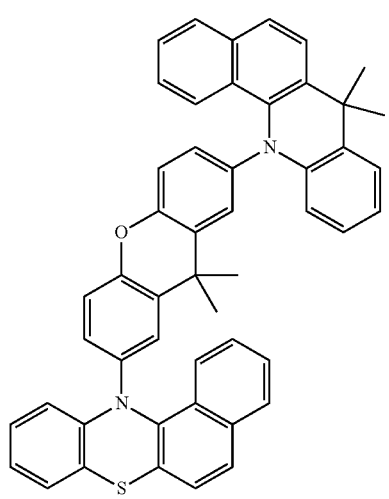
TD-22
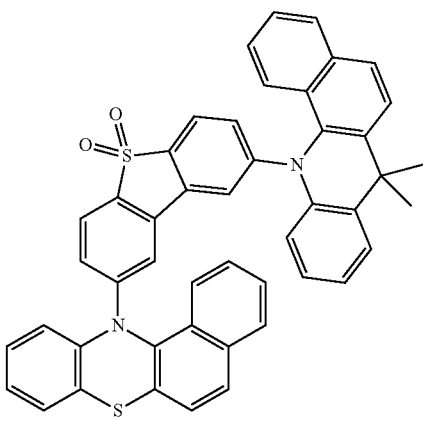
TD-23
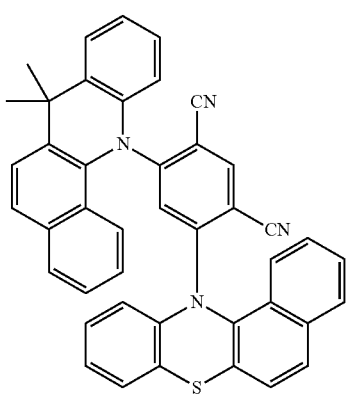
TD-24
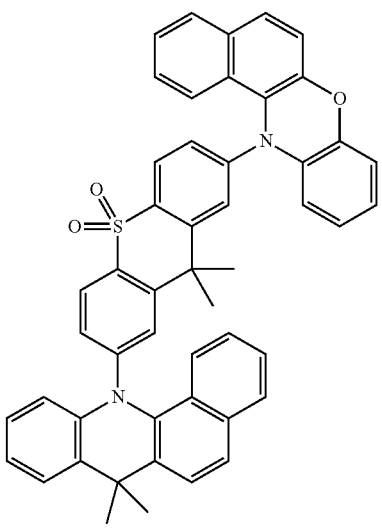

TD-25
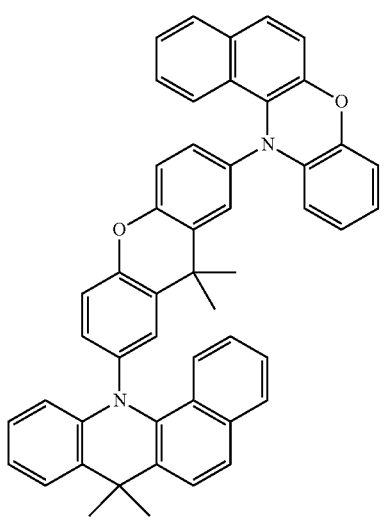
TD-28
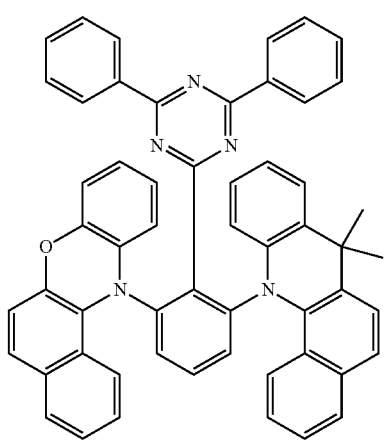
TD-26
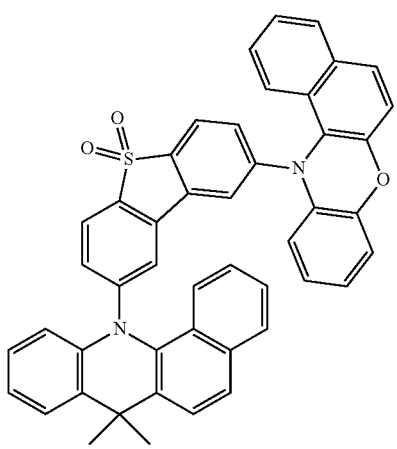
TD-29
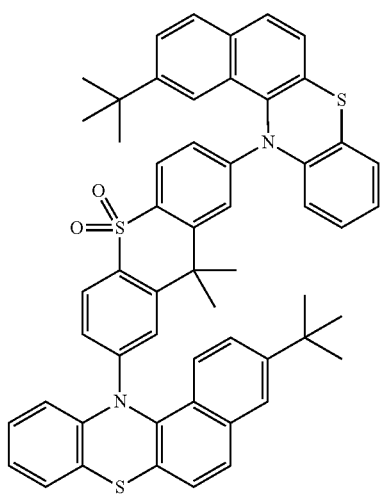
TD-27
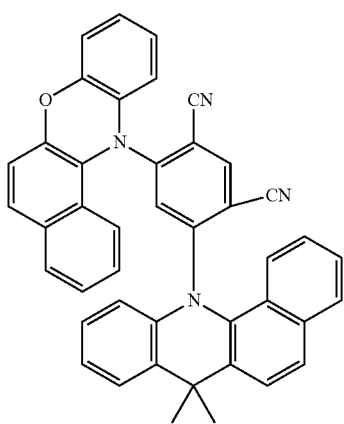
TD-30
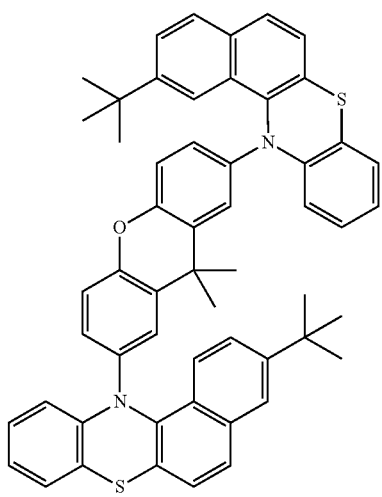

TD-31
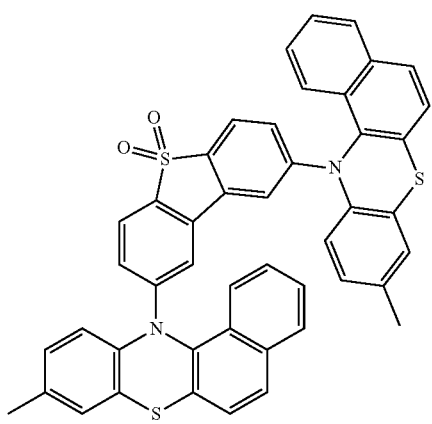
TD-34
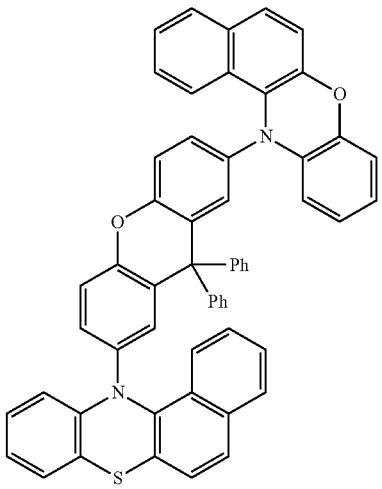
TD-32
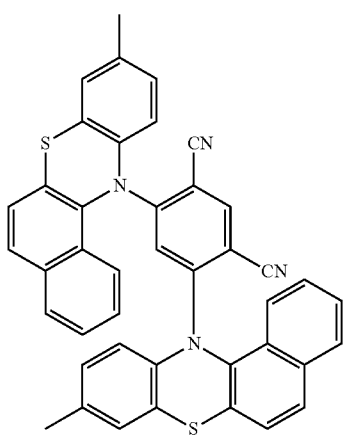
TD-35
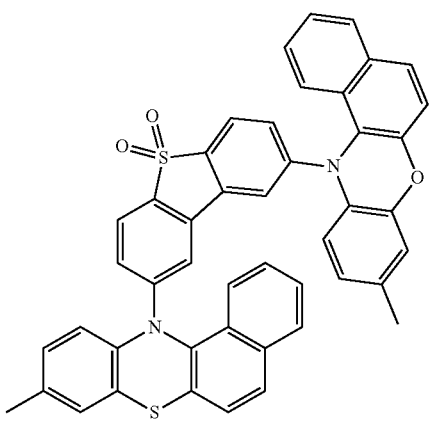
TD-33
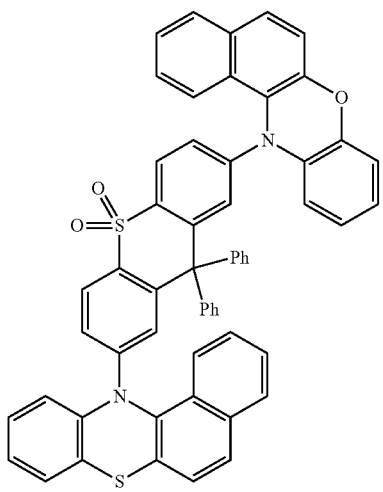
TD-36
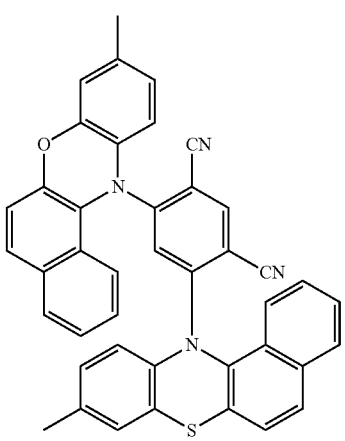

TD-37
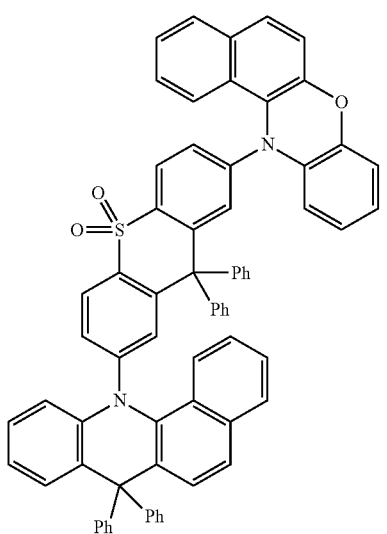
TD-38
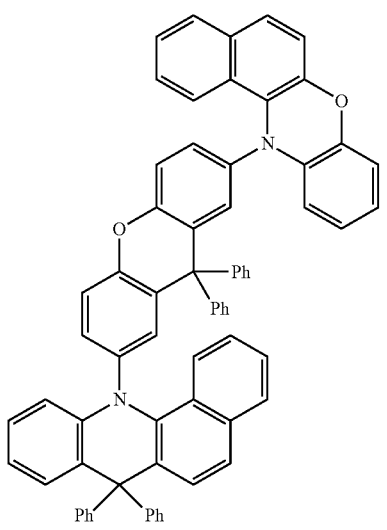
TD-39
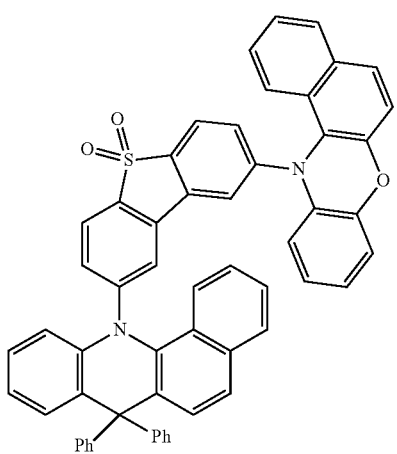
TD-40
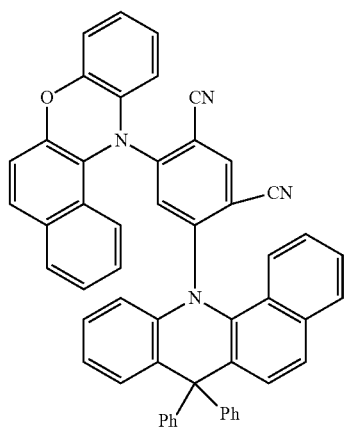
TD-41
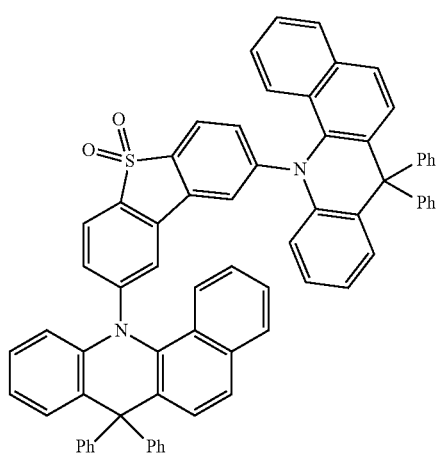
TD-42
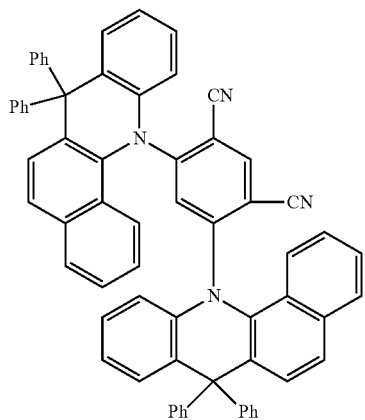

-continued
TD-43
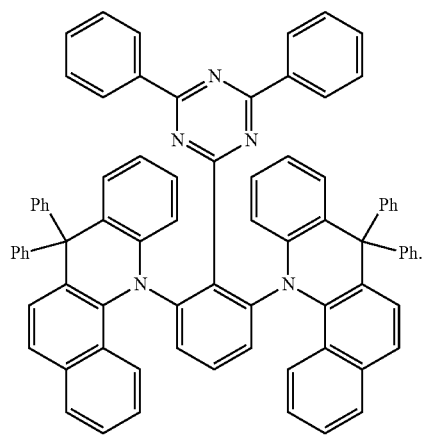
* * * * *